United States Patent
Hart et al.

(10) Patent No.: US 9,594,071 B2
(45) Date of Patent: *Mar. 14, 2017

(54) DEVICE AND METHOD FOR LASER ANALYSIS AND SEPARATION (LAS) OF PARTICLES

(71) Applicants: Sean J. Hart, Alexandria, VA (US); Alexander V. Terray, Alexandria, VA (US); Colin G. Hebert, Laurel, MD (US)

(72) Inventors: Sean J. Hart, Alexandria, VA (US); Alexander V. Terray, Alexandria, VA (US); Colin G. Hebert, Laurel, MD (US)

(73) Assignee: Colin G. Hebert, Laurel, MD (US)

(*) Notice: Subject to any disclaimer, the term of this patent is extended or adjusted under 35 U.S.C. 154(b) by 722 days.

This patent is subject to a terminal disclaimer.

(21) Appl. No.: 13/954,654

(22) Filed: Jul. 30, 2013

(65) Prior Publication Data

US 2014/0220557 A1 Aug. 7, 2014

Related U.S. Application Data

(63) Continuation-in-part of application No. 11/962,541, filed on Dec. 21, 2007, now Pat. No. 8,529,760.

(Continued)

(51) Int. Cl.
*B01D 21/00* (2006.01)
*B01L 3/00* (2006.01)
(Continued)

(52) U.S. Cl.
CPC ..... *G01N 33/4833* (2013.01); *B01D 21/0009* (2013.01); *B01L 3/502761* (2013.01);
(Continued)

(58) Field of Classification Search
CPC .. G01N 1/40; G01N 2001/4038; G01N 21/63; G01N 21/64; G01N 21/6428;
(Continued)

(56) References Cited

U.S. PATENT DOCUMENTS 3,826,364 A * 7/1974 Bonner ................ B07C 5/3425
209/3.1
3,960,449 A * 6/1976 Carleton ............ G01N 15/1434
250/574

(Continued)

OTHER PUBLICATIONS

Mark M. Wang, Eugene Tu, Daniel E. Raymond, Joon Mo Yang, Haichuan Zhang, Norbert Hagen, Bob Dees, Elinore M. Mercer, Anita H. Forster, Ilona Kariv, Philippe J. Marchand & William F. Butler; Microfluidic sorting of mammalian cells by optical force switching, Nature Biotechnology; Jan. 2005; 83-87; vol. 23 No. 1; Genoptix, Inc., San Diego, CA.

(Continued)

*Primary Examiner* — Joseph Drodge
(74) *Attorney, Agent, or Firm* — US Naval Research Laboratory; Suresh Koshy

(57) ABSTRACT

A device and method for particle separation. The device includes at least one collimated light source operable to generate at least one collimated light source beam. The device further includes a first channel in a first plane and a focused particle stream nozzle operably connected to the first channel. The device further includes a second channel in a second plane orthogonal to the first plane. The second channel communicates with the first channel. The second channel comprises a second channel cross-section. The second channel is oriented to receive the collimated light source beam. The device further includes a third channel in a third plane orthogonal to the second plane. The third channel communicates with the second channel. The collimated light source beam is oriented to enter a cross-section (Continued)

of the first channel, then to pass through the second channel, and then to enter a cross-section of the third channel.

20 Claims, 18 Drawing Sheets

Related U.S. Application Data

(60) Provisional application No. 61/677,524, filed on Jul. 31, 2012.

(51) Int. Cl.
  G02B 3/00    (2006.01)
  G02B 5/00    (2006.01)
  G01N 15/00   (2006.01)
  G01N 33/48   (2006.01)
  G01N 33/483  (2006.01)
  G01N 15/14   (2006.01)
  G01N 15/02   (2006.01)

(52) U.S. Cl.
  CPC .... B01L 3/502776 (2013.01); G01N 15/1404 (2013.01); *B01L 2200/0636* (2013.01); *B01L 2200/0652* (2013.01); *B01L 2300/0816* (2013.01); *B01L 2300/0864* (2013.01); *B01L 2300/0887* (2013.01); *B01L 2400/0454* (2013.01); *B01L 2400/0487* (2013.01); *G01N 2015/0288* (2013.01); *G01N 2015/1415* (2013.01)

(58) Field of Classification Search
  CPC ........... G01N 21/6439; G01N 21/6441; G01N 21/6486; G01N 15/14; G01N 15/1404; G01N 15/1409; G01N 15/1411; G01N 15/1415; G01N 15/1434; G01N 15/1436; G01N 15/1452; G01N 15/149; G01N 2015/0288; G01N 2015/1409; G01N 2015/1411; G01N 2015/1415; G01N 2015/1452; G01N 2015/149; G01N 33/483; G01N 33/4833; B01L 3/5027; B01L 3/502753; B01L 3/502776; B01L 3/502761; B01L 2200/0636; B01L 2200/0652; B01L 2300/0816; B01L 2300/0864; B01L 2400/0454; B01L 2300/0887; B01L 2400/0487; B01L 3/00; G02B 3/00; G02B 3/02; G02B 3/06; G02B 5/00; G02B 5/08; G02B 5/0808; G02B 5/0816; G02B 5/10; H01J 3/14; H01J 3/16; H01J 3/26; H01J 3/28; B01D 21/00; B01D 21/0009
  USPC ...... 209/1, 155; 210/748.01, 748.06, 748.09, 210/767; 250/222.2, 251, 396 R, 250/397–400; 356/36–38, 73, 335–343, 356/432, 441, 442; 359/51, 54, 69; 385/116, 117; 422/82.05, 82.07, 82.08, 422/82.11; 435/4, 6.1, 7.1, 7.2, 7.21, 435/7.23, 34, 39, 287.1, 287.2, 287.3, 435/288.7, 288.5
  See application file for complete search history.

(56) References Cited

U.S. PATENT DOCUMENTS

| | | | | |
|---|---|---|---|---|
| 5,495,105 A * | 2/1996 | Nishimura | ............... | H05H 3/04 250/222.2 |
| 6,506,609 B1 * | 1/2003 | Wada | ................. | B01F 13/0062 422/50 |
| 6,778,724 B2 * | 8/2004 | Wang | ...................... | H05H 3/04 385/16 |
| 6,815,664 B2 * | 11/2004 | Wang | ...................... | B07C 5/34 250/251 |
| 7,758,811 B2 * | 7/2010 | Durack | ................ | C12N 5/0612 422/67 |
| 8,529,760 B1 * | 9/2013 | Hart | ...................... | B01J 19/121 204/600 |
| 8,552,363 B2 * | 10/2013 | Erickson | ........... | B01L 3/502761 250/251 |
| 8,753,891 B2 * | 6/2014 | Hart | ................... | B01D 21/0009 209/1 |
| 2002/0058332 A1 * | 5/2002 | Quake | .............. | B01L 3/502761 435/288.5 |
| 2005/0067337 A1 * | 3/2005 | Hart | ...................... | B01J 19/121 210/143 |
| 2007/0095669 A1 * | 5/2007 | Lau | ......................... | B03C 5/005 204/547 |
| 2007/0269345 A1 * | 11/2007 | Schilffarth | ......... | G01N 15/1484 422/73 |
| 2008/0208511 A1 * | 8/2008 | Trainer | ............. | G01N 15/0205 702/128 |
| 2009/0176271 A1 * | 7/2009 | Durack | ................ | C12N 5/0612 435/40.5 |

OTHER PUBLICATIONS

Pamela T. Korda, Michael B. Taylor & David G. Grier, Kinetically Locked-In Colloidal Transport in an Array of Optical Tweezers; The American Physical Society, Physical Review Letters, Sep. 16, 2002; 128301-1/ 128301-4; vol. 89, No. 12; Chicago, Il.

Sang Bok Kim, Jin Ho Kim & Sang Soo Kim; Theoretical development of in situ optical particle separator; cross-type optical chromatography, Applied Optics; Sep. 20, 2006; 6919-6924, vol. 45, No. 27; Optical Society of America.

S.C. Grover, A.G. Skirtach, R.C. Gauthier & C.P. Grover, Automated single-cell sorting system based on optical trapping, Journal of Biomedical Optics, Jan. 14-22, 2001, vol. 6, No. 1.

M.P. MacDonald; G.C.Spalding & K. Dholakia, Microfluidic sorting in an optical lattice. Letters to nature, Nov. 27, 2003; Nature Publishing Group, 421-424, Nature, vol. 426.

Takashi Kaneta, Yasunori Ishidzu, Naoki Mishima & Totaro Imasaka, Theory of Optical Chromatography, Analytical Chemistry, Jul. 15, 1997, vol. 69, No. 14; 2701-2710, Hakozaki, Fukuoka 812, Japan.

Robert W. Applegate Jr., Jeff Squier, Tor Vestad, John Oakey, David W. M. Marr, Philippe Bado, Mark A. Dugan & Ali A. Said. Microfluidic sorting system based on optical waveguide integration and diode laser bar trapping. The Royal Society of Chemistry, 2006. 422-426, Lab Chip vol. 6. Golden, CO.

Anita H. Forster, Mark M. Wang, William F. Butler, Mirianas Chachisvilis, Thomas D.Y. Chung, Sadik C. Esener, Jeffrey M. Hall, Osman Kibar, Kristie Lykstad, Philippe J. Marchand, Elinore M. Mercer, Luis M. Pestana, Sudipto Sur, Eugene Tu, Rong Yang, Haichuan Zhang & Ilona Kariv. Use of moving optical gradient fields for analysis of apoptotic cellular responses in a chronic myeloid leukemia cell model; Analytical Biochemistry; 2004, 14-22 vol. 327. Elsevier Inc. San Diego, CA.

Nicholas F. Fell, Jr., Ronald G. Pinnick, Steven C. Hill, Gorden Videen, Stanley Niles, Richard K. Chang, Stephem Holler, Yongle Pan, Jerold R. Bottiger & Burt V. Bronk, Concentration, Size, and Excitation Power Effects on Fluorescence from Microdroplets and Microparticles Containing Tryptophan and Bacteria. N.F.F. Conference, Nov. 1998, 52-63 SPIE vol. 3533, Boston, MA.

Pierluigi Reschiglian, Andrea Zattoni, Barbara Roda, Sonia Casolari, Myeong Hee Moon, Jisun Lee, Jaehong Jung, Kare Rodmalm & Giovanna Cenacchi. Bacteria Sorting by Field-Flow Fractionation. Application to Whole-Cell *Escherichia coli* Vaccine Strains. Analytical Chemistry, Oct. 1, 2002, 4895-4904, vol. 74, No. 19 American Chemical Society.

Alice Gilman-Sachs, Flow. Report, Analytical Chemistry Jul. 1, 1994, 700a-707a. vol. 66, No. 1 American Chemical Society.

(56) References Cited

OTHER PUBLICATIONS

Frances S. Ligler, George P. Anderson, Peggy T. Davidson, Richard J. Foch, Jeffrey T. Ives, Keeley D. King, Greg Page, David A. Stenger & James P. Whelan, Remote Sensing Using an Airborne Biosensor. Environmental Science & Technology, 1998, 2461-2466, American Chemical Society, vol. 32, No. 16.

J.W. Hofstraat, W.J.M Van Zeijl, J.C.H. Peeters & L. Peperzak, Flow cytometry, fast and quantitative characterization of particles in suspension. Analytica Chimica Acta, 1994, 135-145, vol. 290; Elsevier Science B.V. Amsterdam.

Karl-Gustav Wahlund & J. Calvin Giddings, Properties of an Asymmetrical Flow Field-Flow Fractionation Channel Having One Permeable Wall. Analytical Chemistry, May 1, 1987; 1332-1339, vol. 59, No. 9, American Chemical Society.

\* cited by examiner

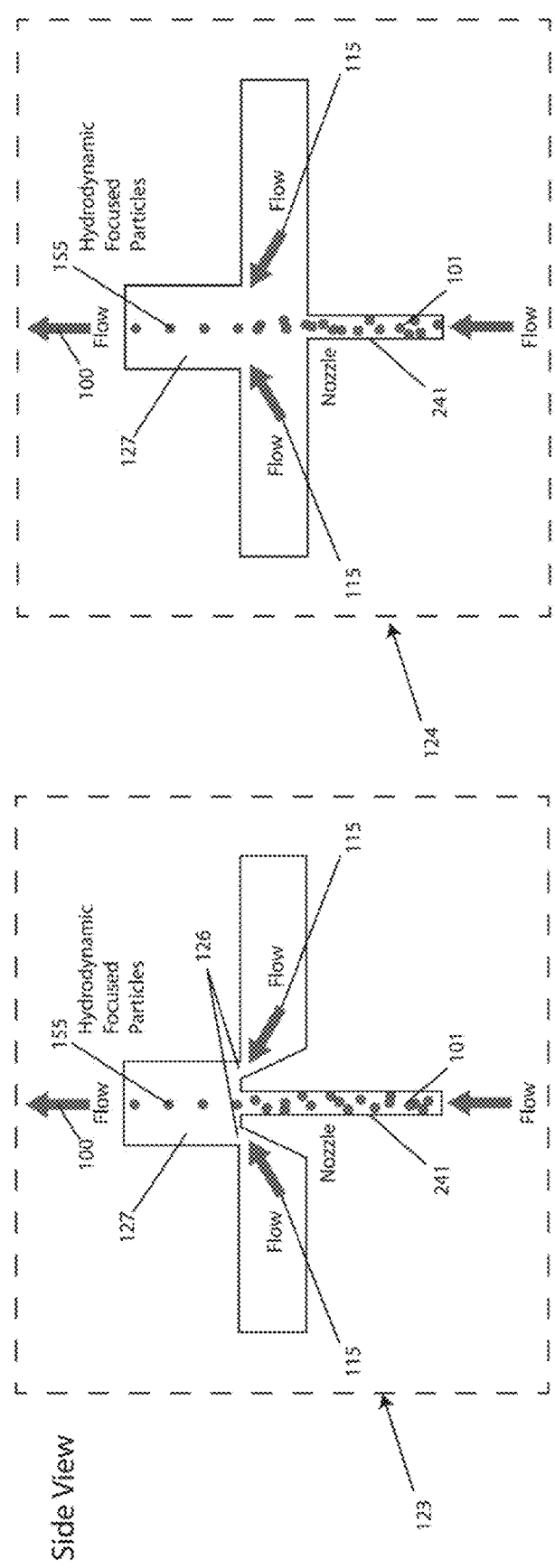

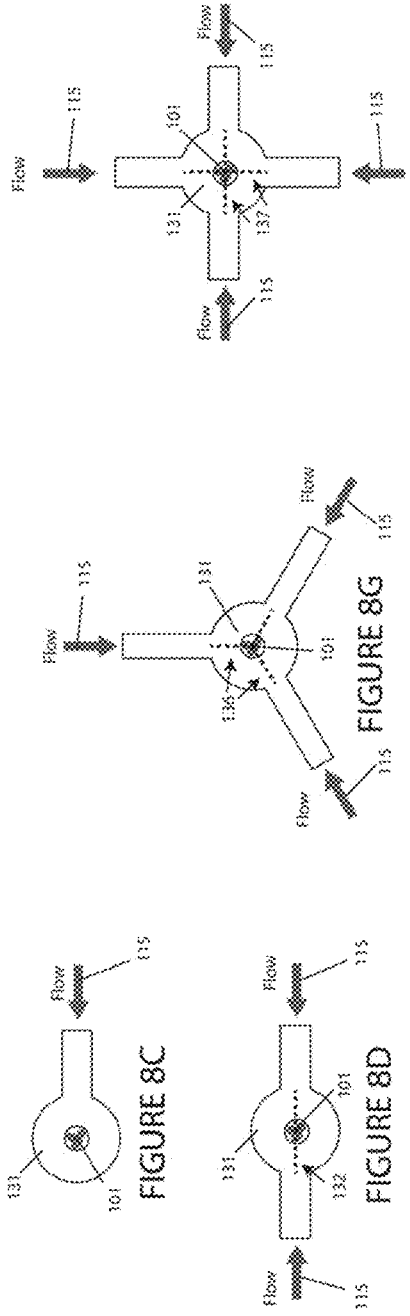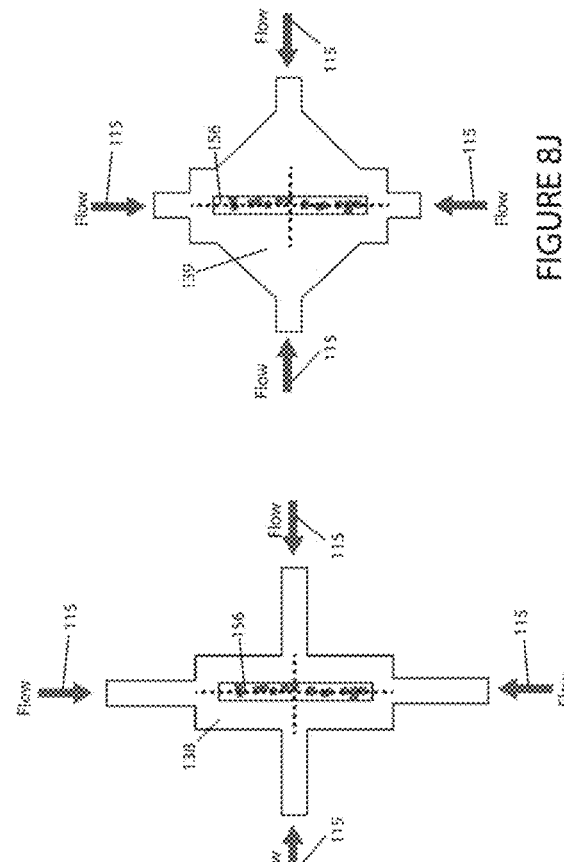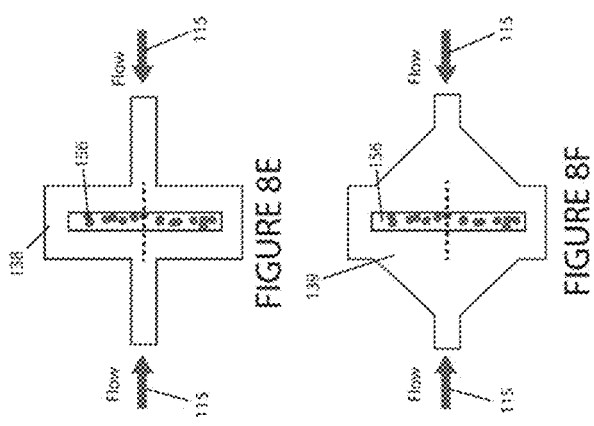

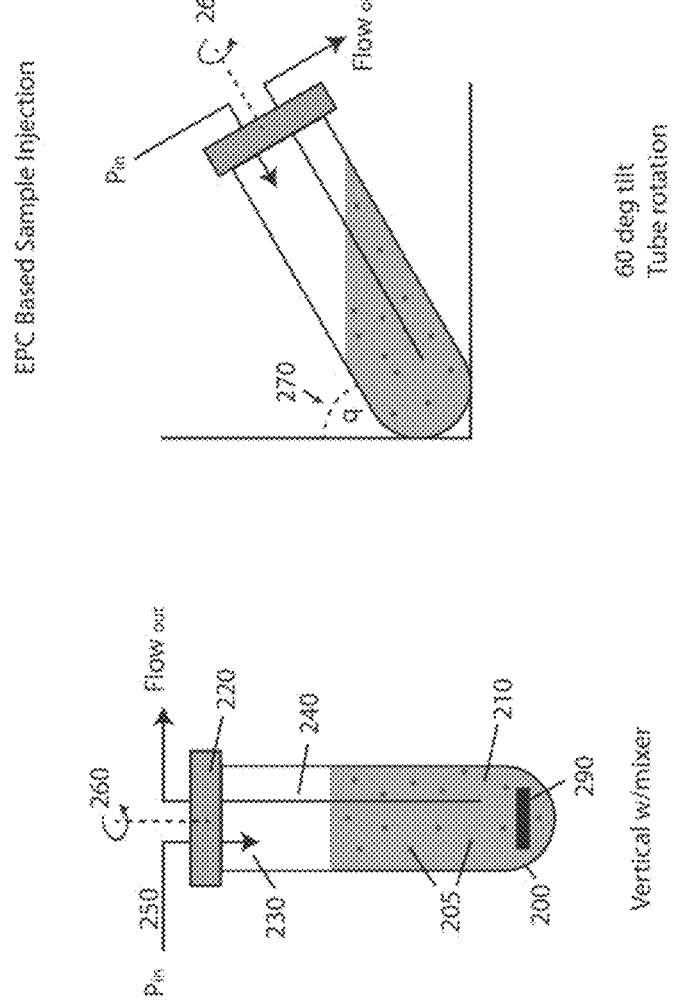

Quick tube connect/disconnect with integrated pneumatic pumping

Tube without lid or septum    Tube with septum

Bonded Five Layer Fused Silica Microfluidic Device
400

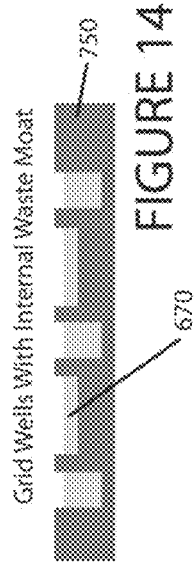
Liquid Level Below Well Top
FIGURE 14A
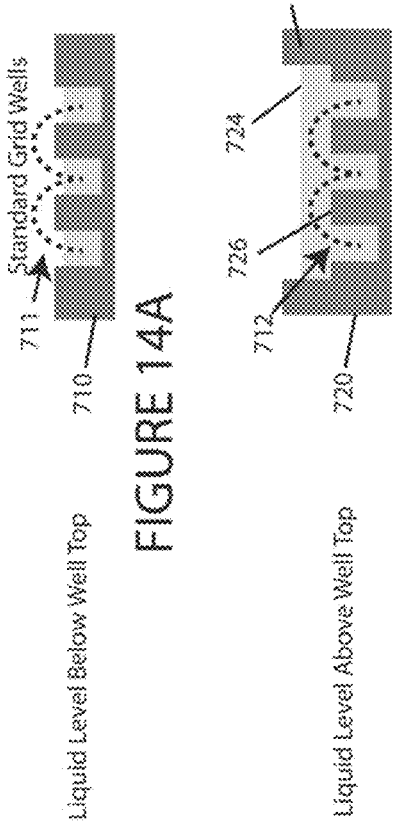
Liquid Level Above Well Top
FIGURE 14B
FIGURE 14C
Removable Polymer Base
FIGURE 14D
Removable Microfluidic Network Base
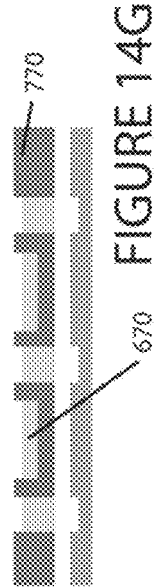
Grid Wells With Internal Waste Moat
FIGURE 14E
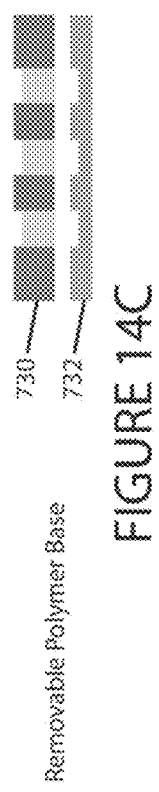
FIGURE 14F
FIGURE 14G
FIGURE 14H

DEVICE AND METHOD FOR LASER ANALYSIS AND SEPARATION (LAS) OF PARTICLES

CROSS-REFERENCE TO RELATED APPLICATIONS

The present application claims priority to U.S. Provisional Patent Application Ser. No. 61/677,524, which was filed on 31 Jul. 2012. Additionally, the present application is a continuation-in-part application of U.S. patent application Ser. No. 11/962,541, which was filed 21 Dec. 2007.

BACKGROUND OF THE INVENTION

Field of the Invention

This invention relates in general to a device and method for particle separation for fluids, and in particular to a device and method for particle separation for fluids using optical pressure.

Description of the Related Art

The invention of the laser has made possible many new areas of research and technology. Unique optical properties allowing a laser to be highly focused have made detailed studies of radiation pressure possible. Most important is the laser's ability to focus down to a tiny spot size, resulting in a large photon density. This large number of photons translates into a significant amount of radiation force applied to a particle in the beam path. Radiation pressure has been used to trap and direct particles caught in the focus of a laser beam. Manipulation of the beam focus and beam position can be used to move particles into desired positions and configurations. The types of objects that have been optically trapped include glass and polymer spheres, viruses, bacteria, and biological cells. Recently, size-based separation of particles flowing in a fluid opposite to the direction of laser propagation has been achieved.

In recent years, a technique has been developed, termed laser separation, which involves optical-force-based separation of differently sized particles in the 1-10 micron range. When particles in a liquid flowing within a capillary encounter a laser beam propagating in the opposite direction, the particles are subjected to optical pressure near the beam focal point (i.e., the region of highest photon density) intense enough to impart momentum sufficient to overcome fluid drag forces. The result is that particles in the fluid become trapped and move against the fluid flow until the beam diverges and the photon density decreases. The particles remain stationary when the optical pressure equals the force exerted on the particles by the liquid flow (i.e., Stoke's force).

For a sphere of refractive index $n_2$ in a medium of lower refractive index, $n_1$, the force due to optical pressure of the laser, $F_{optical\_pressure}$, is given by equation 1:

$$F_{optical\_pressure} = \frac{2n_1 P}{c}\left(\frac{a}{\omega}\right)^2 Q^*, \qquad (1)$$

where P is the power of the laser, c is the speed of light, a is the sphere radius, $\omega$ is the beam radius, and $Q^*$ is the conversion efficiency of optical radiation pressure to Newtonian force on the particle. The term $(n_1 P/c)$ defines the incident momentum per second in a medium of refractive index $n_1$. The dimensionless parameter, $Q^*$ defines the conversion efficiency of optical pressure transfer arising from light reflection and refraction based upon geometrical considerations and is calculated using the Fresnel reflection and transmission coefficients, which in turn depend upon $n_2$, the refractive index of the particle.

Separation in a liquid flow is measured by the distance particles travel away from the focal point against the fluid flow. This distance traveled is the optical retention distance, z: the point at which the optical pressure equals the force exerted on the spheres by the liquid molecules and is defined, according to Equation 2:

$$z = \frac{\pi \omega_0^2}{\lambda}\sqrt{\frac{n_1 P Q a}{3\pi \eta v c \omega_0} - 1}, \qquad (2)$$

where P is the power of the $TEM_{00}$ mode laser, c is the speed of light, a is the sphere radius, $\omega_0$ is the beam radius at the focal point, $\lambda$ is the wavelength of light, v is the velocity of the particle in the water flow, and $n_1$ is the viscosity of water. The refractive index of the particle is used in the calculation of the efficiency of optical pressure transfer, Q.

Optical pressure has been used extensively in research and industry for biological size-based micromanipulation. The chemical effect on optical pressure in bacteria has been observed: small chemical differences in the surface coatings have been shown to result in large force differentials on different strains of the same species of non-pathogenic bacteria. However, the theoretical chemical dependence, development, and use of optical pressure chemical differentials for separation have not yet been demonstrated.

BRIEF SUMMARY OF THE INVENTION

Applicants have determined that there is a significant need to develop clinical and research instrumentation capable of sorting cell streams for detection of pathogens and disease that are sensitive, selective, automated, and cost/size effective. An embodiment of the current invention is a laser-force-based separator that does not rely on antibodies, or fluorescent molecules for cell disease identification, selection, and sorting. Rather, it utilizes inherent differences in optical pressure, which arise from variations in particle size, shape, refractive index, or morphology, as a means of separating and characterizing particles. Optical pressure occurs when photons reflect and refract through a transparent particle and impart momentum. In practice, cells are injected into a microfluidic device and directed into a near-infrared laser beam that exerts a physical force on the cells, which is then measured. The magnitude of the force on each cell is related to the intrinsic properties of the cell and varies across cell types and for differing diseases.

In an embodiment of the instant invention, a fluidic device for optical analysis and separation of particles has been developed using flow channels that can be constructed using a variety of materials. This embodiment of the instant invention uses fluid flow to propel particulate samples through a network of fluidic channels. At one or more locations in the fluidic network, laser light is introduced to the channels to interact with the particles and impart optical force via radiation pressure. This force when balanced against the fluidic drag on the particles results in changes in particle velocity that can be used to identify differing particles or changes with populations of particles based on intrinsic differences. The fluidic and optical force balance can also be used to change the relative position of particles to one another based upon their intrinsic properties thus resulting in physical separations among the laminar layers within the fluidic flow channels.

Another embodiment of the invention includes a device for particle analysis and/or separation. The embodiment of the invention includes at least one collimated light source operable to generate at least one collimated light source beam. The at least one collimated light source beam includes at least one beam cross-section. The embodiment of the invention includes a first channel in a first plane. The embodiment of the invention includes a second channel in a second plane orthogonal to the first plane. The second channel communicates with the first channel. The second channel includes a second channel cross-section. The second channel is oriented to receive the collimated light source beam. The embodiment of the invention includes a third channel in a third plane orthogonal to the second plane. The third channel communicates with the second channel. The collimated light source beam is oriented to enter a cross-section of the first channel, then to pass through the second channel, and then to enter a cross-section of the third channel. The embodiment of the invention includes a focused particle stream nozzle operably connected to the first channel.

Another embodiment of the instant invention includes a method of particle separation. At least one collimated light source operable to generate at least one collimated light source beam is provided. The at least one collimated light source beam includes at least one beam cross-section. A body is provided and defines a first channel in a first plane, a second channel in a second plane orthogonal to the first plane, the second channel communicating with the first channel, the second channel comprising a second channel cross-section, the second channel being oriented to receive the at least one collimated light source beam, a third channel in a third plane orthogonal to the second plane, the third channel communicating with the second channel. The at least one collimated light source beam is transmitted through the second channel, the transmitted at least one collimated light source beam comprising a beam direction. A sample flow is transmitted into the first channel. The fluid sample includes a flow direction opposite the beam direction. The sample flow includes a plurality of particles. The plurality of particles includes at least one particle type. The sample flow includes a sample flow cross-section. The sample flow cross-section includes a sample flow cross-section size. The sample flow includes a sample flow center. At least one sheath flow is transmitted into the first channel, a combined flow including the sample flow and the at least one sheath flow. Focusing the sample flow cross-section size within the combined flow and/or positioning the sample flow center within the combined flow.

The possibility of separating chemically different particles according to an embodiment of the instant invention offers important new possibilities for analysis and possible purified collection of colloidal samples such as organic particulates, inorganic particles (e.g., glass and metal particles), and biological species such as cells, bacteria, and viruses. Differentiation of biological samples such as bacteria is based upon chemical differences in their capsules. Polysaccharides, lectins, lipoteichoic acids, and proteins are some of the biomolecules present in various bacterial species and strains. It is well known that there exists a substantial range of refractive indices in bacterial and viral samples due to their different chemical compositions. The ability to separate biological species based upon physical and chemical properties using only light interaction with samples in a simple fluid flow is new and has great potential benefits when applied to bio-warfare detection and biomedical analysis. Not only are samples physically separable using light, but from their position in the separation field one can determine their refractive index. Thus, from a predicted location one may identify specific entities in an unknown mixture. When samples are optically retained against a glass surface, such as when occurs using the microfluidic step function type device, the extent to which they are deformed (i.e., squished) against the glass wall by the force of the laser is related to their composition and mechanical structure. This has immediate implications for biological cells that are affected by disease such as cancer which is known to directly affect the cytoskeleton of cells. Erythrocytes undergo stretching and compression which depends on their age; older erythrocytes being less flexible. The potential for analysis of disease states in biological system (e.g., cells and small tissue samples) is very large.

BRIEF DESCRIPTION OF THE DRAWINGS

FIG. 2 is a conceptual elevation view of a generalized embodiment of the instant invention, provided to show the principle of its operation when a collimated light source is on.

FIG. 3 is a conceptual elevation view of another generalized embodiment of the instant invention, provided to show the principle of its operation when a collimated light source is on.

FIGS. 8A-8B are elevational views of alternative illustrative focused particle stream nozzles according to illustrative embodiments of the instant invention.

FIGS. 8C-8J are plan views of alternative focused particle stream nozzles according to illustrative embodiments of the instant invention.

FIGS. 9A-9G are plan views of illustrative sample reservoirs according to illustrative embodiments of the instant invention.

FIGS. 14A-14H are plan views of alternative well designs according to illustrative embodiments of the instant invention.

DETAILED DESCRIPTION OF THE INVENTION

Figure 1:
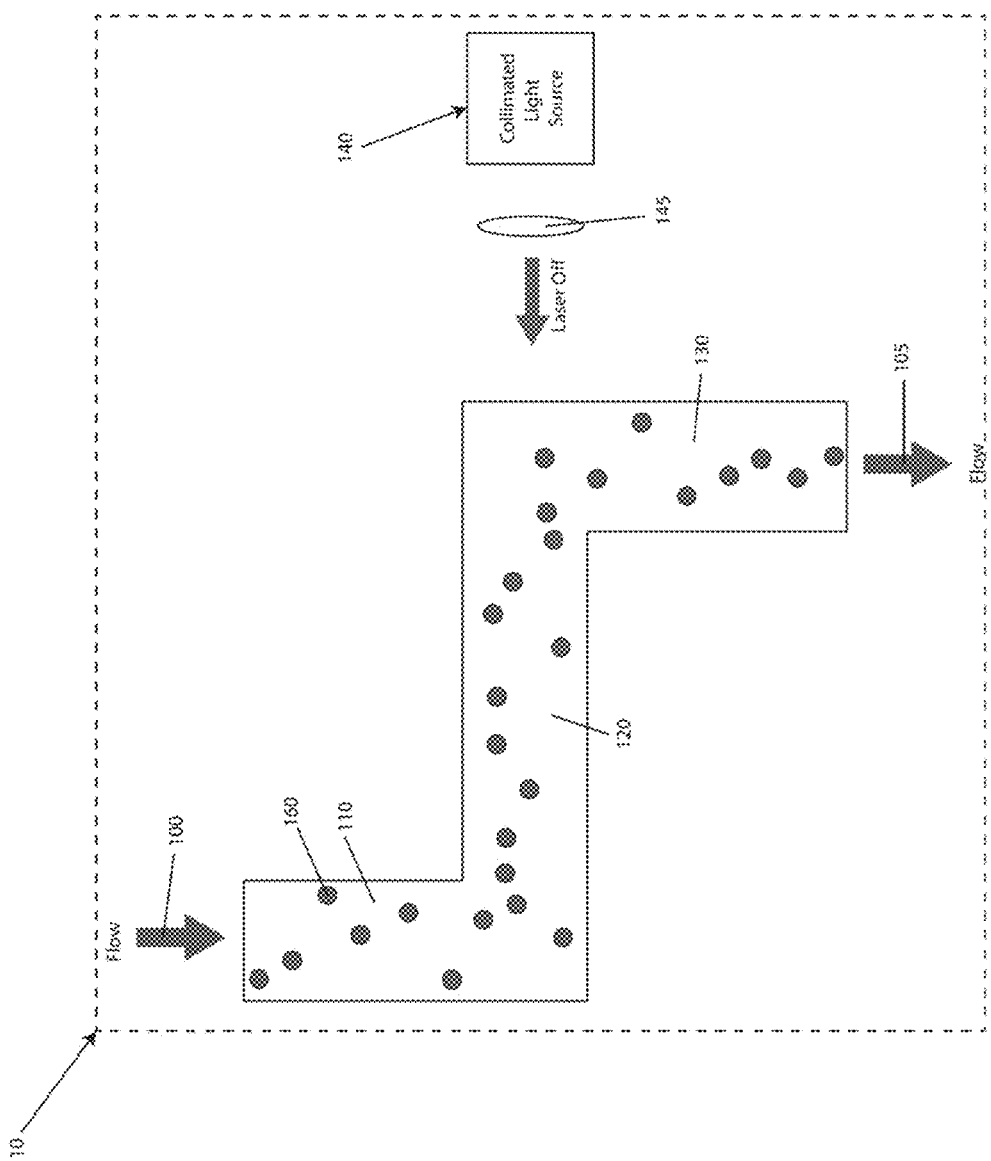
FIG. 1 is a conceptual elevation view of a generalized embodiment of the instant invention, provided to show the principle of its operation when a collimated light source is off.

An embodiment of the invention includes a device for particle analysis and/or separation 10. This embodiment is described as follows with reference to FIGS. 1-6. The embodiment of the invention includes at least one standard collimated light source 140 operable to generate at least one collimated light source beam. The at least one collimated light source beam includes at least one beam cross-section. The embodiment of the invention includes a first channel 110 in a first plane. The embodiment of the invention includes a second channel 120 in a second plane orthogonal to the first plane. The second channel 120 communicates with the first channel 110. The second channel 120 includes a second channel cross-section. The second channel 120 is oriented to receive the collimated light source beam. The embodiment of the invention includes a third channel 130 in a third plane orthogonal to the second plane. The third channel 130 communicates with the second channel 120. The collimated light source beam is oriented to enter a cross-section of the first channel 110, then to pass through the second channel 120, and then to enter a cross-section of the third channel 130. The embodiment of the invention includes a focused particle stream nozzle 111 operably connected to the first channel 110, for example, as shown in FIG. 6.

Figure 2:
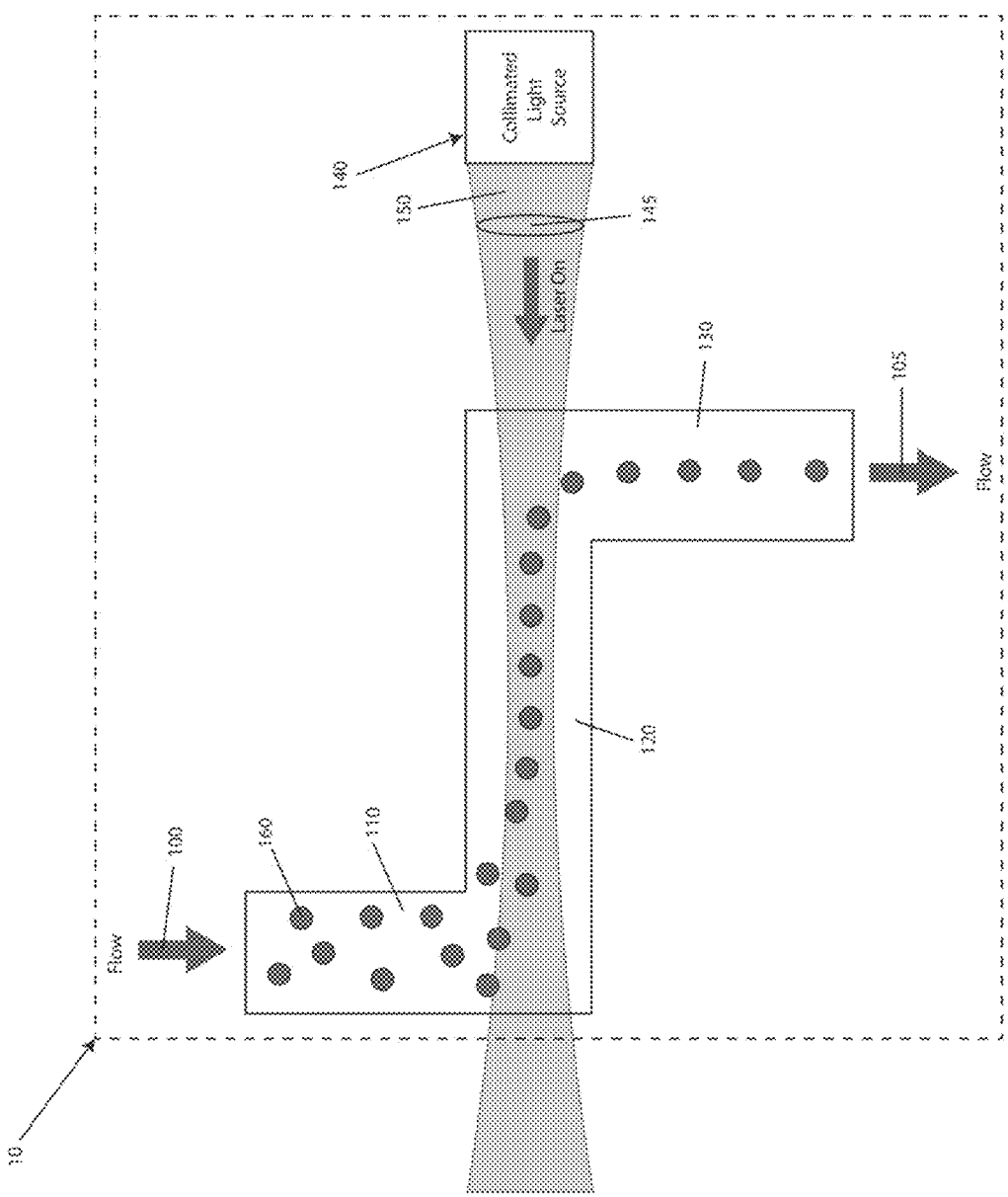

In FIG. 1, a fluid flow 100 containing particles 160 is directed through a first channel 110, followed by a second orthogonal channel 120 and a third channel 130 parallel to the first channel 110. The direction of the fluid flow is given by the flow arrows 100 & 105. A laser 140 is present with a focusing lens element 145 but not emitting a beam in FIG. 1, and particles 160 are evenly distributed throughout the flow channels. FIG. 2 depicts the invention with the laser 140 operating, emitting a laser beam 150, directing the beam through a focusing lens element 145 into the second flow channel 120. The particles are aligned within the laser beam 150 due to the gradient force which draws particles toward the region of highest laser intensity. The laser scatter force propels particles in the direction of laser beam 150 propagation (e.g., right to left in terms of FIG. 2).

Figure 3:
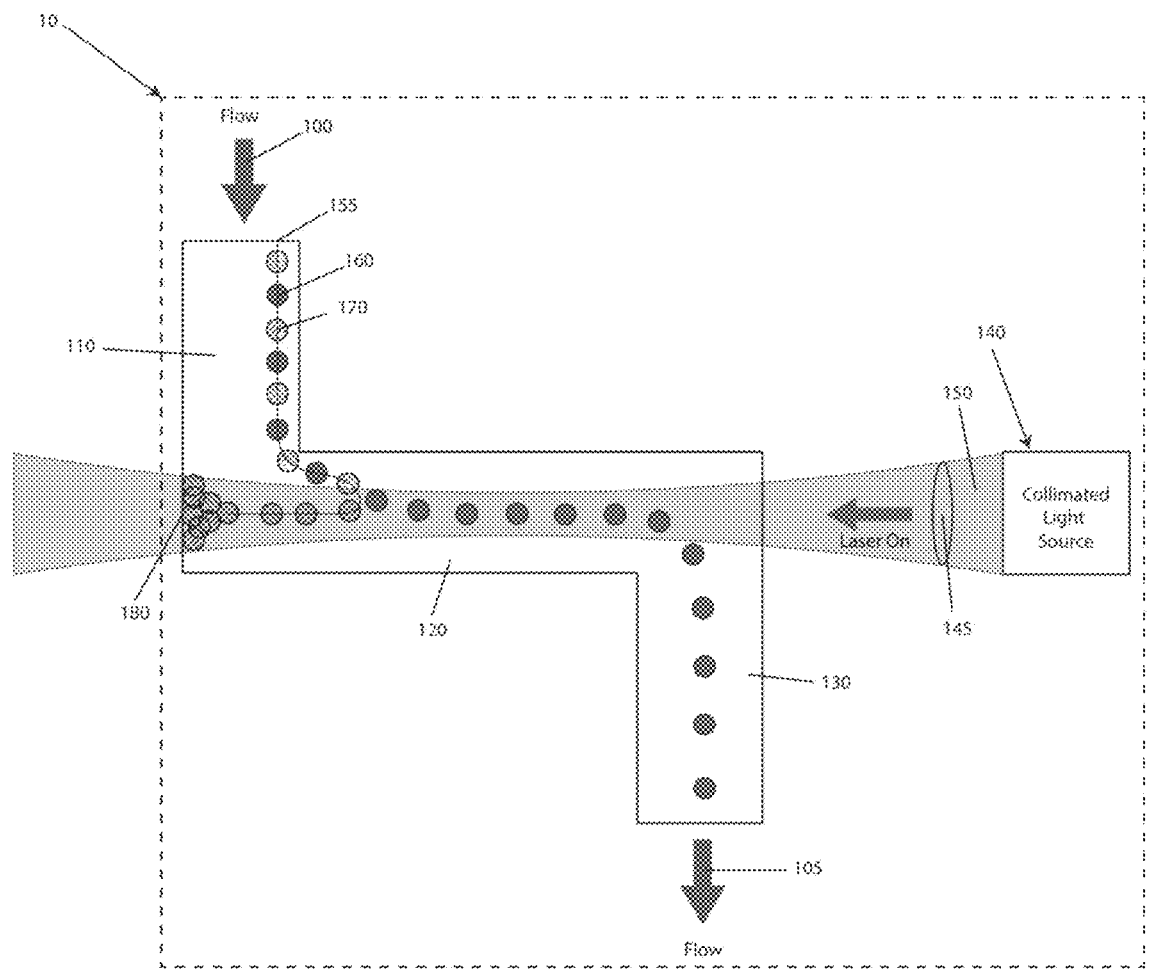

In FIG. 3, particle separation is shown by a process in which a focused stream 155 enters the first flow channel 110 aligned close to the channel wall nearest to the second channel entrance containing two particle types 160, 170 of differing optical force properties (e.g., due to size, shape, refractive index, morphology, local refractive index structure, other standard inherently physical property, or a standard induced property). When the particle stream 155 enters the second channel 120 and encounters the laser beam 150 particles with higher optical force 170 are forced by the laser pressure against the fluid flow upstream to a resting place against the wall 180 of the first channel 120 where they remain until the laser power is reduced or removed. The particles with lower optical force 160 continue downstream in the second channel 120 and then into the third channel 130 thus effecting a separation of the two differing particle types.

Figure 4:
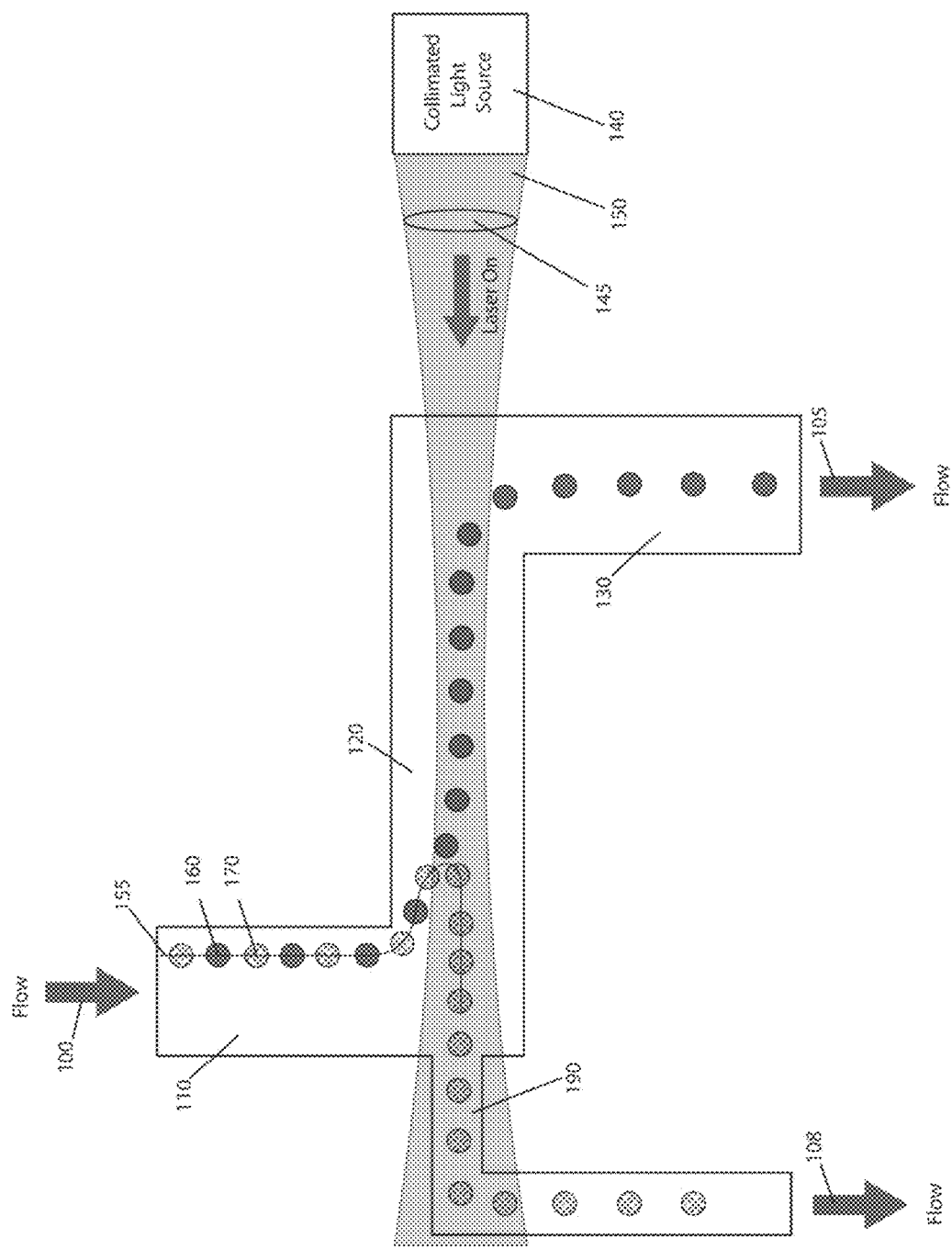
FIG. 4 is a conceptual elevation view of an embodiment of the instant invention, showing, for example, at least one collection channel.
Figure 5:
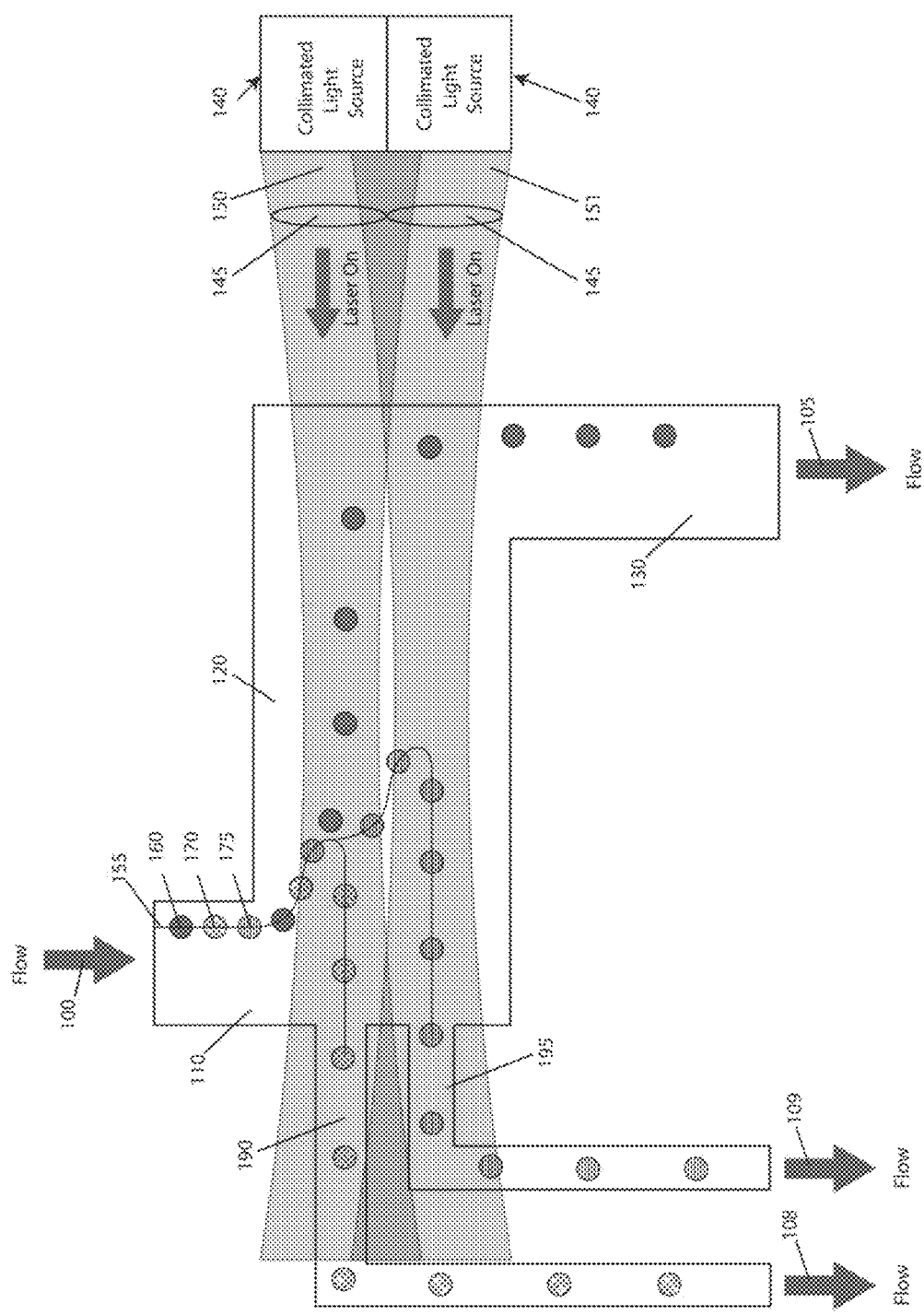
FIG. 5 is a conceptual elevation view of an embodiment of the instant invention, showing, for example, a plurality of collection channels and a plurality of collimated light sources.
Figure 6:
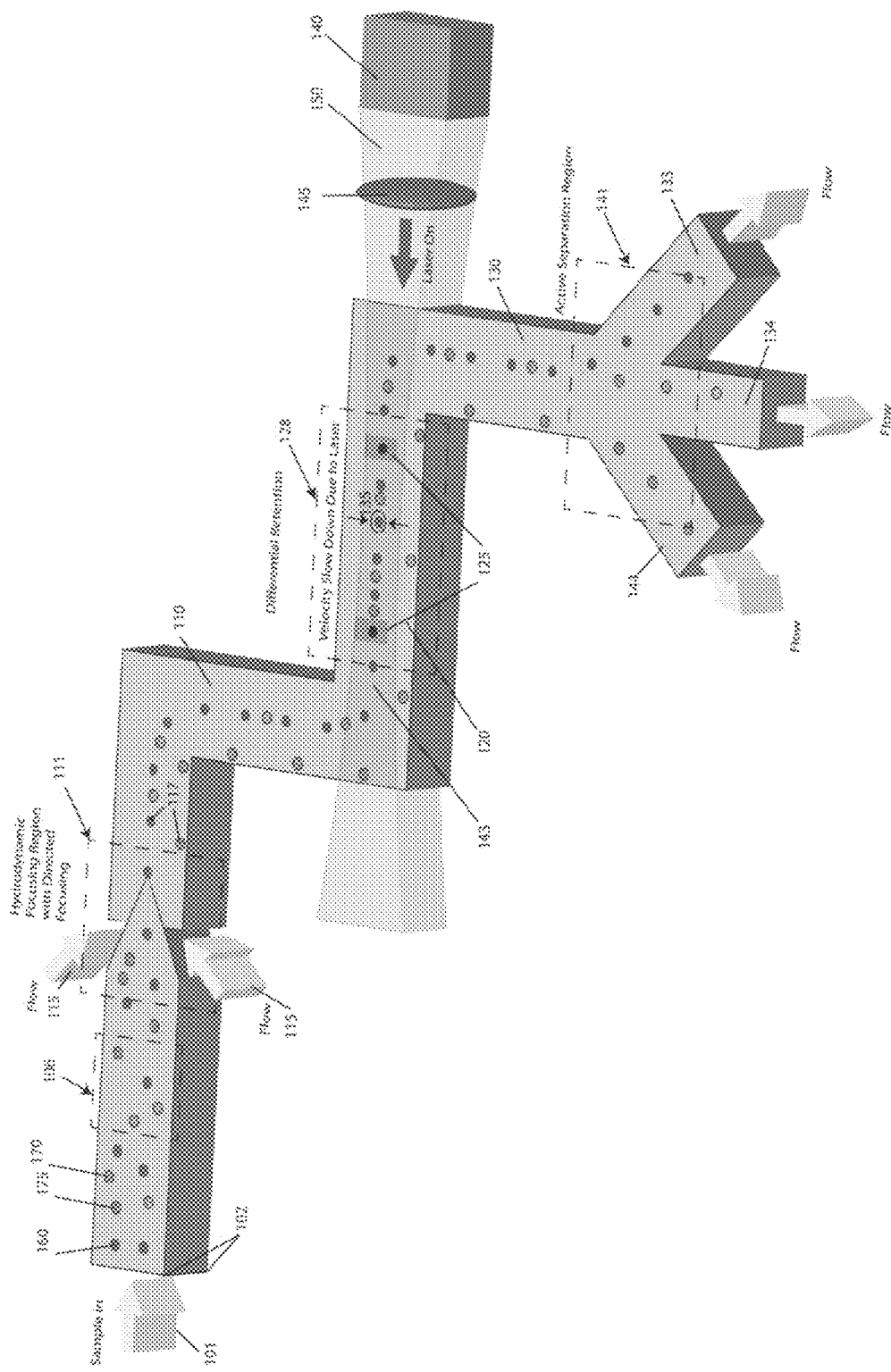
FIG. 6 is a perspective view of an embodiment of the instant invention, showing, for example, a plurality of collection channels and a focused particle stream nozzle.

Optionally, the embodiment of the invention further includes at least one collection channel communicating with the second channel, for example, as shown in FIGS. 4 and 5. Optionally, the at least one collection channel includes a plurality of collection channels, for example, as shown in FIG. 5. Two collection channels are shown for ease of illustration. But, it should be understood that the exact number of collection channels may be more or less, as determined by the application at hand by one of ordinary skill in the art. Optionally, the at least one collimated light source 140 includes a plurality of collimated light sources that correspond to the plurality of collection channels, for example, as shown in FIG. 5.

In FIG. 4, an opening 190 is introduced into the wall structure where the first channel 110 meets the second channel 120 and is connected to another channel to carry separated particles away from the first channel 110. In this embodiment, particles 170 are forced by the optical pressure into the exit channel 190 and are then carried away by flow 108 for collection or further analysis.

FIG. 5 illustrates a more complex embodiment of the invention relative to the one depicted in FIG. 4. FIG. 5 shows two exit channels 190, 195 that accept optically pushed particles and two laser beam regions 150, 151. A focused stream 155 enters the first flow channel 110 aligned close to the channel wall nearest to the second channel entrance containing three particle types 160, 170, 175 of differing optical force properties. When the particle stream 155 enters the second channel 120 and encounters the first laser beam 150 particles with higher optical force 170 are forced by the laser pressure against the fluid flow upstream into exit channel 190, where they are then carried away by flow 108 for collection or further analysis. Particles experiencing lower optical force 160 exit the system while particles with intermediate optical force are slightly retained and enter the second beam region with higher optical laser power and are then propelled upstream into a second exit channel 195, and are then carried away by flow 109 for collection and analysis. The laser beam regions are created in any of a variety of standard ways, such as by employing two separate standard lasers, standard diode laser bars, standard laser(s) coupled into standard fiber optics, etc. and used with standard optics, such as plano-convex, achromatic, aspheric, cylindrical, axicon, objective or other standard lens types. A single beam that is scanned between the two regions can create a similar effect using a standard piezo-electric mirror, a standard spatial light modulator, a standard acousto-optic modulator, or other standard light manipulation device.

Optionally, the embodiment of the invention further includes a plurality of collection channels 144, 133, 134 communicating with said third channel, for example, as shown in FIG. 6. Three collection channels are shown for ease of illustration. But, it should be understood that the exact number of collection channels may be more or less, as determined by the application at hand by one of ordinary skill in the art.

FIG. 6 shows this embodiment of the invention as including a multistage microfluidic device with a shallow channel depth 102, not less than 1 micron and not more than the width of the channel. Incoming sample 101 enters a particle interrogation region or unit 106. Interrogation by the particle interrogation unit 106 includes, for example, a standard brightfield imaging method, a standard light scatter detection method, a standard single wavelength or spectroscopic fluorescent detection method, a standard Raman detection method, or other standard optical detection methods. The sample then enters a hydrodynamic focusing region or unit 111 with multiple sheath flows (e.g., 2-6 separate sheath flow regions) 115. The sheath flows are independently controlled resulting in a hydrodynamic focusing region capable of directing focused samples 117 spatially and in response to information from the previous sample interrogation. The focused samples continue down the channel 110 and enter the differential retention region or unit 128. Differential retention refers to the difference in retention time (i.e., time required to travel the same linear distance in the laser beam) or velocity difference between two or more particles 160, 170 as they are slowed by optical force traveling within the path of the laser beam 150 in the microfluidic channel 120. The particles could pass through at the same or different moments in time. Retention time generally is the amount of time a particle spends in the channel, and more specifically can be measured by defining two or more reference points in the channel 125 and measuring the time it takes for a particle to travel between these points. The retention time of a particle is dependent upon a number of factors, including size, shape, and refractive index, morphology, local refractive index structure, or other inherent physical property and can be used as a means of differentiating between different types of particles. The laser beam 150 used in the differential retention region can consist of all previously mentioned types, shapes, patterns, power and intensity variations. Of the spatially focused particles, only those in the center of the channel 143 are interrogated, the others pass through and exit into a waste channel 144. Information is gathered in the differential retention region. Real time analysis of this information is used to actively direct exiting particles to one or more specific exit channels 133, 134 in the active separation region 139. The exit flow direction and distribution are controlled via manual or automatic fluid valves, electronic pressure control of air pressure above sealed fluid exit reservoirs or other flow control methods.

An alternative embodiment of the embodiment of the invention shown in FIG. 6 is a static mode where the particle is stopped at a specified differential retention location 135 by balancing the optical and fluidic forces. Rather than measuring velocity in this region a flow sensor is used to measure the flow rate at which each particle stops in the flow for a given laser power. Because the optic and fluidic forces are balanced the Stokes drag force (i.e., from flow rate and channel dimension) is equal to the optical force. The properties of each cell can be measured sequentially in this manner. Although not a high throughput measurement system, this embodiment of the invention allows close observation and imaging of the trapped cell and also dynamic changes in optical force resulting from biochemical or biological changes in a cell. Reagent streams containing chemicals, biochemicals, cells, or other standard biological agents can be introduced into the flow channels to interact with the trapped cell(s). Thus dynamic processes can be quantitatively monitored by measuring changes in optical force during experiments on a single cell or cells.

Optionally, the embodiment of the invention further includes at least one particle interrogation unit 106 communicating with the second channel 120, for example, as shown in FIG. 6. The particle interrogation unit 106 includes a standard illuminator, standard optics, and a standard sensor. Optionally, the at least one particle interrogation unit 106 includes a standard bright field imager, a standard light scatter detector, a standard single wavelength fluorescent detector, a standard spectroscopic fluorescent detector, a standard CCD camera, a standard CMOS camera, a standard photodiode, a standard photomultiplier tube, a standard photodiode array, a standard chemiluminescent detector, a standard bioluminescent detector, and/or a standard Raman spectroscopy detector.

Figure 7:
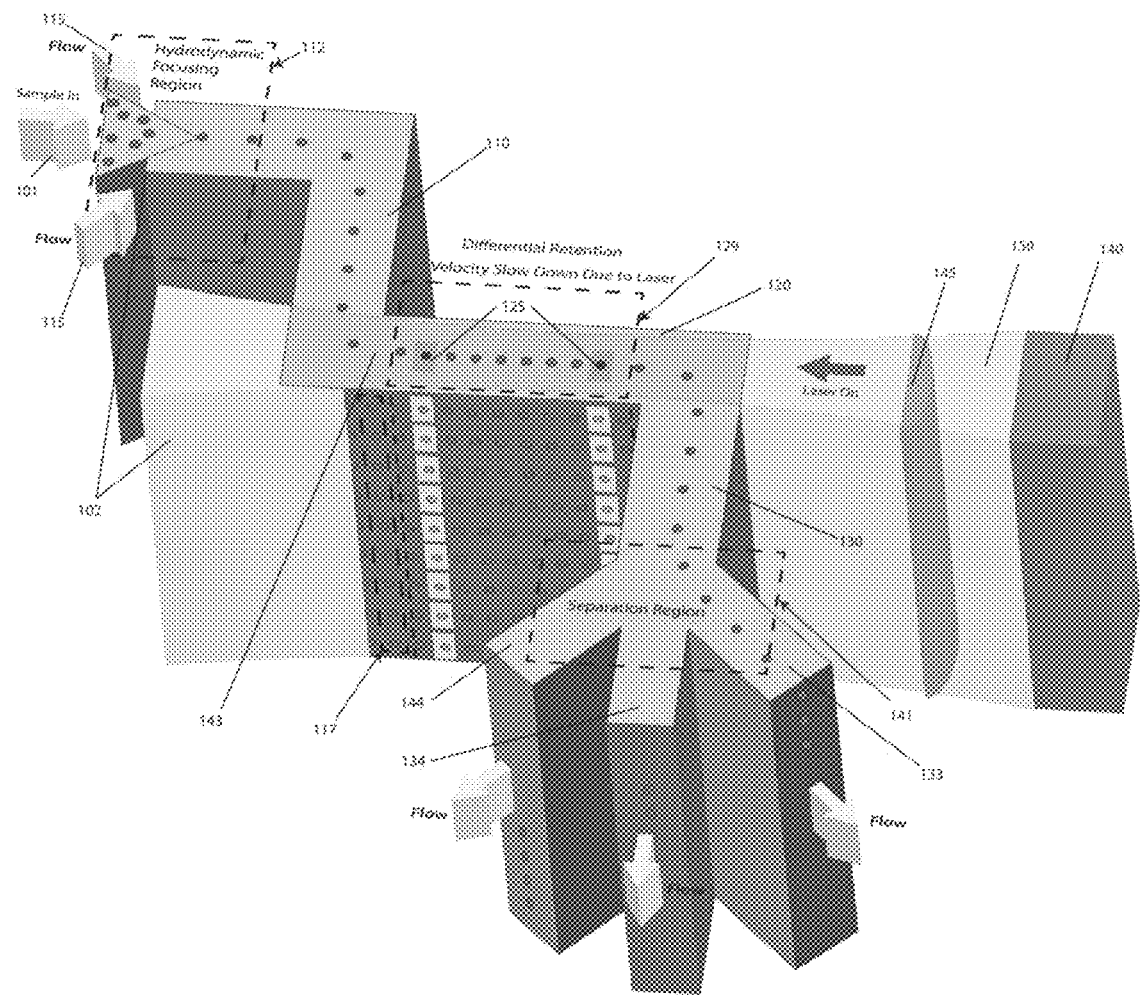
FIG. 7 is a perspective view of an embodiment of the instant invention, showing, for example, an optical element and a second channel having sufficient depth to allow multiple particle streams to be interrogated, identified, and/or separated.

The embodiment of the invention shown in FIG. 7 includes a multistage microfluidic device, with a deep channel depth 102, not less than the width of the channel. Incoming sample 101 is hydrodynamically focused into the first channel 110. The focused sample core flow and sheath flows 115 are elongated due to the deep dimension of the channel structure. The result of the deep dimension is that the core flow is transformed into a slit geometry and the sheath flows focus this core flow into a focused sheet 117, including particles suspended in the sample. The sample sheet enters the differential retention region 129 where particles across the entire depth of the focused sample experience different optical and fluidic forces depending on their location in the flow profile, optical field and response to the resulting forces. As in the shallow device shown illustratively in FIG. 6, the laser beam 150 may consist of all previously mentioned types, shapes, patterns, powers and intensity variations. The laser beam can be made to interrogate all particles in the entire focused sheet 117. As in a single retention region, for example, as shown in FIG. 6, particle velocity changes in response to the balance of fluid and optical forces on a particle are used to garner information about a sample. Expanding this process to a deep dimension device, multiple simultaneous retention analysis can be conducted and this information used to direct exiting particles to specific channels using previously mentioned standard methods (e.g., pneumatically controlled flow, conventional valves, switches, actuators, etc.).

Optionally, the focused particle stream nozzle 111 includes at least one sheath flow channel and a sample injection inlet 241 connected to the at least one sheath flow channel, for example, as shown in FIG. 7 and FIGS. 8A-J.9. Optionally, the focused particle stream nozzle 111 includes at least one junction between the at least one sheath flow channel and the sample injection inlet, such as shown in FIGS. 8A and 8B. Optionally, the at least one sheath flow channel are tapered toward said at least one junction, such as shown in FIG. 8A.

The hydrodynamic focusing of particles suspended in a solvent is another feature of this embodiment of the invention, and illustrative alternative hydrodynamic focusing units are shown in FIGS. 8A-J. Hydrodynamic focusing occurs when higher rate sheath flow is directed around a lower rate core flow. If particles are entrained in the incoming sample flow 101 the particles are also hydrodynamically focused within the flow 100. Each design involves a sample flow 101 and at least one sheath flow 115. At the junction point where these sheath flows combine, a taper 126 can be used (such as shown in FIG. 8A), but is not required (such as shown in FIG. 8B). The side views show two these two alternatives, one with a taper 123 and one without 124. Alternative top views are presented in FIGS. 8C-8J, each illustrating a different approach. A single sheath flow 115 is optionally combined with a circular disk region 131, with an outer diameter larger than the combined channel 127, for example, as shown in FIG. 8C. Two sheath flow channels 115 can be combined with the circular disk region 131, for example, as shown in FIG. 8D. With two independent sheath flow channels, the balance of these flows can be used to direct the final position of focused particles in the combined channel 127, but only in one direction across the combined channel cross-section 132. With three independent sheath flow channels 115, for example, as shown in FIG. 8E, the hydrodynamically focused stream can be effectively positioned anywhere in the exit channel cross-section 136. As with three sheath flows (115), four sheath flows can also be combined to effectively position the hydrodynamically focused stream anywhere in the exit channel cross-section 137, for example, as shown in FIG. 8E. Other than the circular sample flow 101, other shapes can be used, such as a slit or rectangular channel 156, for example, as shown in FIGS. 8E-8H. With a slit shaped core design, a hydrodynamically focused sheet of particles can be formed. This core design can be combined with two or four inlet sheath channels 115. The junction where the inlet sheath channels are combined can be rectangular 138 or tapered 139 and again used with two or four inlet sheath flows 115, depending on the amount of positional control desired.

Optionally, the embodiment of the invention further includes at least one sheath flow driver communicating with said at least one sheath flow channel; and a sample flow driver communicating with the sample injection inlet. Optionally, the at least one sheath flow driver includes a sheath flow fluid pressure driver and controller. The sample flow driver includes a sample flow fluid pressure driver and controller. The at least one sample flow driver is independent of the sheath flow driver.

Figures 9F, 9G:
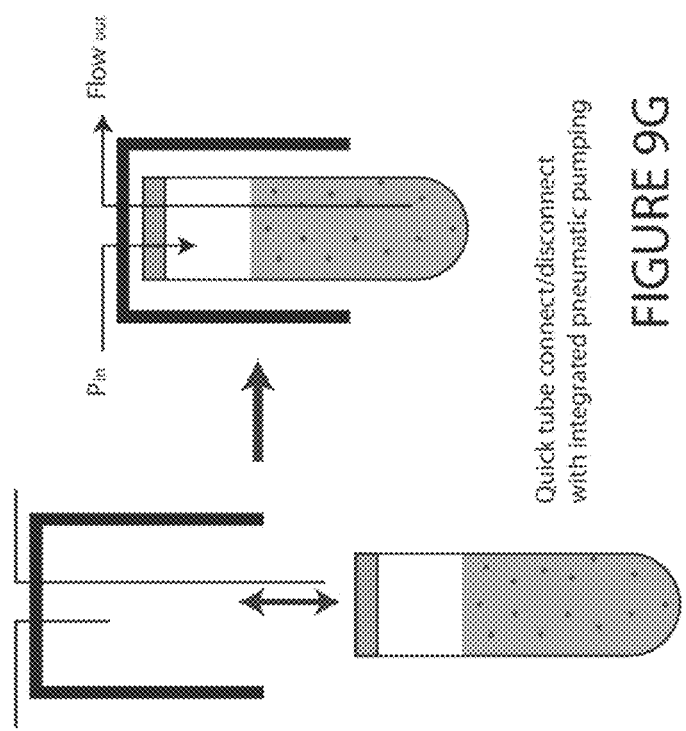

Optionally, the embodiment of the invention further includes a sample reservoir 200 communicating with the sample injection inlet 240. The sample reservoir 200 is connected to the fluid pressure driver and controller. Optionally, the sample reservoir 200 is rotatable, vertically-oriented, tilted, and/or horizontally-oriented, for example, as shown in FIGS. 9A-9C. Optionally, the sample reservoir 200 includes a mixer 290. The mixer 290 includes a stir bar, a microfluidic mixer, an impeller, or a plurality of baffles.

Pressure-based sample injection is described in further detail as follows with reference to FIGS. 9A-9C. The vessel 200 is filled with a sample 205 in a fluid 210 and seals to a lid 220. Prior to attachment to the lid 220, the vessel 200 can be either open to the air 223 or sealed with a septum 225. This lid 220 contains two connections, one for a fluid such as a gas 230 and one for liquid 240. In the septum case 225, the lid connections will be designed such that they can pierce the septum in such a way as to maintain the seal. The gas connection 230 extends through the lid 220 and into the vessel 200 but ends above the surface of the fluid 210 and allows gas to enter or exit the vessel 200. The liquid connection 240 extends through the lid 220 and also ends below the surface of the sample fluid 210. This allows inlet gas 250 to come into the vessel 200 and create an internal pressure that forces fluid into the liquid connection 240 and out of the vessel 200. The pressure of the inlet gas 250 can be adjusted precisely to control the rate of sample injection. Further, the entire vessel 200 can be rotated about its central axis 260 in order to keep the particles 160, 170, 175 in the sample 205 from settling to the bottom of the vessel 200. The vessel 200 can also be titled at an angle from the vertical 270 ranging from 0 to 90 degrees, in either a dynamic or static fashion and in conjunction with rotation 260, in order to keep the sample 205 from settling to the bottom of the vessel 200. The liquid connection 230 can be curved at the bottom 280 to facilitate operation when the vessel 200 is operated with a tilt 270. Also, when operated with a tilt 270, the vessel will rotate independently of the gas 230 and liquid 240 connections. Finally, a mixer 290 such as a stir bar can be included in the bottom of the vessel 200 to help mix the sample. The pneumatic injection system can be used for injecting particles suspended in liquid or can inject liquid alone for the purpose of liquid pumping or delivering chemical/biochemical reagents to samples already in the microfluidic device.

Optionally, the embodiment of the invention further includes a fluid pressure line 250 communicating with said sample flow fluid pressure driver and controller; and a sample inlet line 240. The sample reservoir 200 comprises a septum 220. The fluid pressure line 250 and the sample inlet line 240 pass through the septum 220. Optionally, the sample reservoir 200 includes a sample well plate 590. The sample well plate includes a plurality of sample grid wells and/or a plurality of waste moats. Illustrative, alternative well plates are shown in FIGS. 13A-13D and FIGS. 14A-14H. Optionally, the sample reservoir comprises a sample border wall 722 bordering the sample well plate 590, said sample well plate being recessed relative to said sample border wall, for example, as shown in FIG. 14C. Optionally, the at least one sample well plate 590 includes a sample detachable base 732, 742 and a sample grid plate 730, 770, 740, 780 defining a plurality of through holes. The sample detachable base 732 is made of, for example, plastic, glass, poly(dimethyl)siloxane, ceramic, and/or metal. Optionally, the sample detachable base 732 includes a microfluidic network 742. The microfluidic network 742 is made of for example, plastic, glass, poly(dimethyl)siloxane, ceramic, and/or metal. Optionally, the embodiment of the invention further includes a pressure vessel surrounding the sample well plate 598.

Optionally, the embodiment of the invention further includes at least one outlet reservoir corresponding to the at least one collection channel. Alternative implementations of the outlet reservoir are the same as those of the sample reservoir discussed above. It should be understood that, in practice, for a given device the implementation of the outlet reservoir chosen for a particular application need not be identical to the implementation of the sample reservoir chosen for that particular application. Optionally, the at least one outlet reservoir comprises an outlet well plate. The outlet well plate includes a plurality of outlet grid wells and/or a plurality of waste moats. Optionally, the at least one outlet reservoir includes an outlet border wall bordering the outlet well plate. The outlet well plate is recessed relative to the outlet border wall. Optionally, the at least one outlet well plate includes an outlet detachable base and an outlet grid plate defining a plurality of through holes. Optionally, the outlet detachable base includes a microfluidic network.

Optionally, the embodiment of the instant invention further includes at least one outlet reservoir corresponding to the at least one collection channel. Optionally, the at least one outlet reservoir includes an outlet well plate. The outlet well plate includes a plurality of outlet grid wells and/or a plurality of waste moats. Optionally, the at least one outlet reservoir includes an outlet border wall bordering the outlet well plate. The outlet well plate is recessed relative to the outlet border wall. Optionally, the at least one outlet well plate comprises an outlet detachable base and an outlet grid plate comprising a plurality of through holes. Optionally, the outlet detachable base comprises a microfluidic network.

Figure 13B:
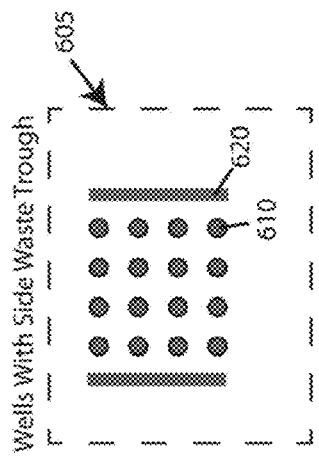
FIGS. 13B-13C are schematic plan views of alternative plate designs according to illustrative embodiments of the instant invention.
Figure 13D:
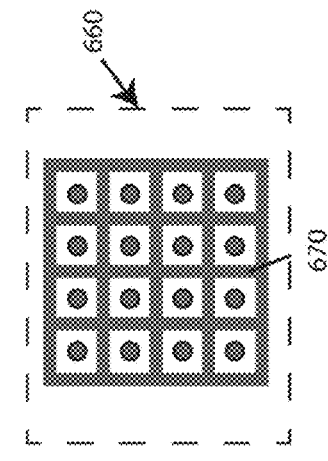
FIG. 13A is a perspective view of a generalized well plate according to an embodiment of the instant invention.
Figure 13A:
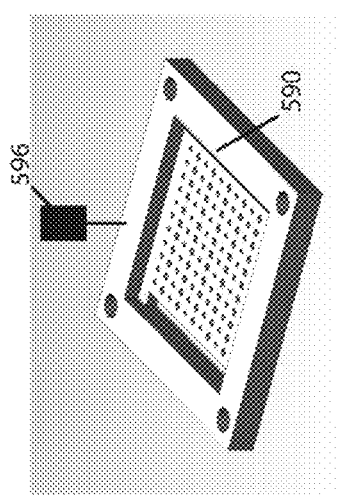
Figure 13C:
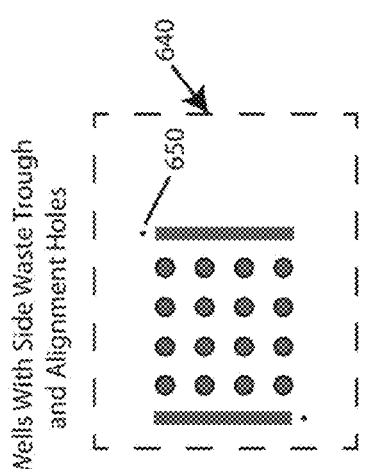

Alternative design details of a well plate 590, shown by way of example in FIGS. 13A-13D and 14A-14H, are optionally used for either sample collection or injection depending on the needed application. Both the plate layout and well design are considered. Looking from above, for example, as shown in FIGS. 13A-13D, the well plate is made up of individual wells 610 that can be filled with liquid arranged in formation along the inside of the plate, as well as waste moats or troughs 620 along the edge of the plate. An array or grid of individual wells 610 can be filled or emptied by addressing the sample tip 596 to that location, while the waste trough 620 can be used as a reservoir for larger volumes of liquid or sample streams. For example, FIG. 13B shows a plate layout 605 wherein the waste moats 620 are located on two sides of the array of wells 610. FIG. 13B shows waste moats on opposite sides of the array of wells 610, an alternative plate layout includes the waste moats on adjacent sides of the array. FIG. 13C shows another plate layout 640, which adds alignment holes 650 at two or more corners of the well plate 590. These alignment holes 650 are used as reference points for the sample tip 596 to improve its accuracy. FIG. 13D shows yet another plate layout 660 still includes individual wells 610, but the waste trough is expanded such that there is a trough 670 between each of the wells. The individual wells 610 are not connected to the waste trough fluidically, but this allows for a much shorter distance from any specific individual well to the waste.

Independent of the plate layout, a number of alternative well designs 710, 720, 730, 740, 750, 760, 770, 780 are optionally used, for example, as shown in FIGS. 14A-14H. FIG. 14A shows a well design 710 including a grid of individual wells 610 that are fluidically independent. To move between wells, the sample tip 596 must break the surface of the liquid following a path similar to the dotted line 711. FIG. 14B shows an alternative well design 720 includes higher plate walls 722, which allow the liquid level 724 to be higher than the top of the wells 726. This well design allows the sample tip 596 to stay below the surface of the liquid as it moves from one well to another 712. FIG. 14C shows an alternative well design 730, which replaces the bottom of the wells with a removable polymer base 732. This base 732 is removable, but creates a liquid-tight seal between the wells 610 when it is attached to the plate 590. The base 732 is optionally a thin plastic film that is rolled onto the bottom of the well plate 590. FIG. 14D shows an alternative well design 740, which also uses a removable polymer base, but contained within the polymer base is a standard network of microfluidic channels 742. These microfluidic channels 742 could connect one well to another or connect the well plate to a reservoir somewhere off chip. Internal waste troughs 670 are optionally added to any of the four above-mentioned well designs 710, 720, 730, 740 to create four additional variations 750, 760, 770, 780, such as shown in FIGS. 14E-14H. Well design 750 is identical to well design 710, except for the addition of the waste troughs between wells, for example, as shown in FIG. 14E. Well design 760 is identical to well design 720, except for the addition of the waste troughs between wells, for example, as shown in FIG. 14F. Well design 770 is identical to well design 730, except for the addition of the waste troughs between wells, for example, as shown in FIG. 14G. Well design 780 is identical to well design 740, except for the addition of the waste troughs between wells, for example, as shown in FIG. 14H.

Figure 10A:
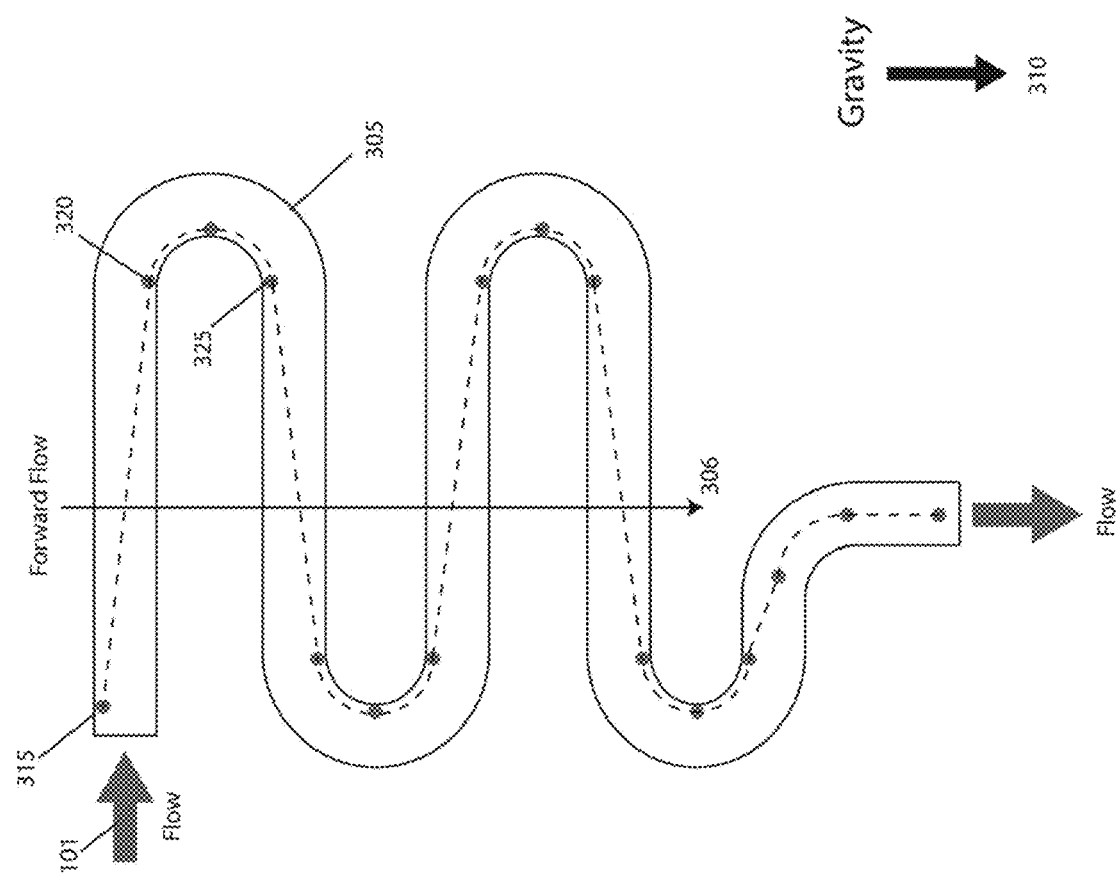
FIGS. 10A-10B are plan views of illustrative serpentine channels according to an embodiment of the instant invention.
Figure 10B:
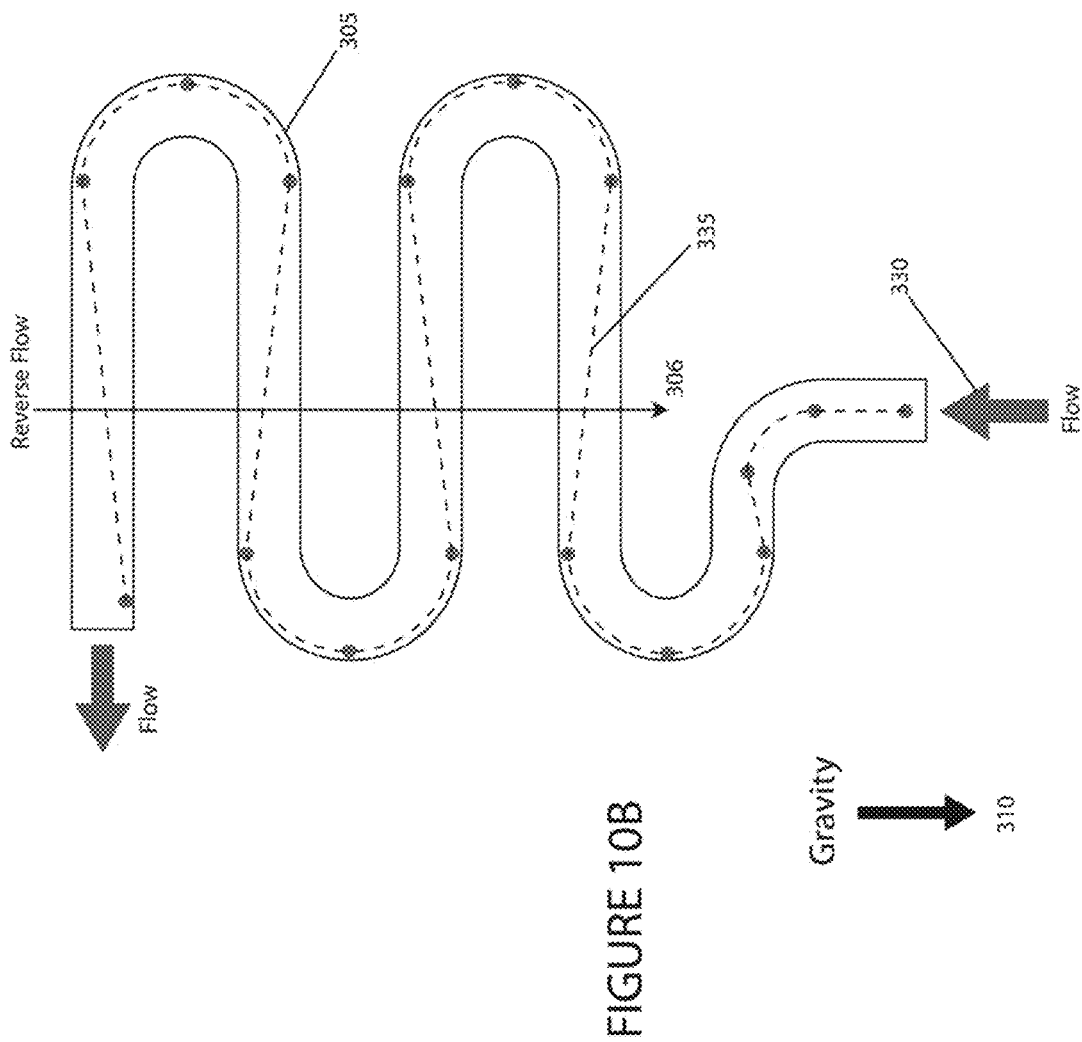

Optionally, the embodiment of the invention further includes a serpentine channel 305, for example, as shown in FIGS. 10A and 10B, connecting the sample reservoir to the sample injection inlet 241. The serpentine channel 305 comprising a plurality of turns and a plurality of lengths, said plurality of lengths comprising a last length and at least one other length, said last length being less than said at least one other length.

Sample delivery is another feature of an embodiment of the invention and alternative designs is illustrated in FIGS. 10A and 10B. FIG. 10A shows forward flowing sample 101 entering a serpentine or zig-zag channel 305, prior to the hydrodynamic and injection nozzle designs discussed previously for FIGS. 6, 7, and 8A-8J. The channel 305 is designed in a serpentine pattern that folds back on itself along its axis 306 that is oriented parallel to the direction of gravity 310. For particles with a density greater than the solvent they are dispersed in, they will settle at a specific rate, finally stopping against the channel bottom surface under static flow conditions. If, during this settling process, the flow is such that a particle that begins at a location at the top surface of the channel 315 reaches a location at the bottom 320, just as the channel turns down parallel with gravity and around the particle, effectively extending settling time for the particle now at a location at the top surface of the channel 325, a particle can be kept entrained in the flowing solvent. By repeating this folding channel design several times, a volume of sample can be kept from settling out and can provide a continuous particulate sample feed. Operating the flow in the reverse direction 330 will accomplish the same result, although particles will follow a different trajectory within the channel 335, for example, as shown in FIG. 10B. By operating the system in a forward flow direction, followed by a reverse flow direction, a sample can be perpetually kept from settling out; this method may also be used to re-suspend previously settled samples. The last length in the channel design can be less than a previous length to introduce the settling particles when they are at the center and highest flow velocity region of the channel.

Optionally, the embodiment of the invention further includes at least one optical element 145 between the at least one collimated light source and said second channel, for example, as shown in FIG. 1, and operable to produce a standard rectangular beam, a standard $TEM_{21}$ mode beam, a standard $TEM_{01}$ mode beam, a standard $TEM_{10}$ mode beam, a standard $TEM_2$, mode beam, a standard Hermite-Gaussian beam mode, a standard Laguerre-Gaussian beam mode, or a standard multimodal beam. Optionally, the at least one optical element 145 includes a standard cylindrical lens, a standard axicon, a standard concave mirror, a standard toroidal mirror, a standard spatial light modulator, a standard acousto-optic modulator, a standard piezoelectric mirror array, a standard quarter-wave plate, and/or a standard half-wave plate.

Optionally, the at least one collimated light source beam includes a standard circularly polarized beam, a standard linearly polarized beam, or a standard elliptically polarized beam.

Figure 11A:
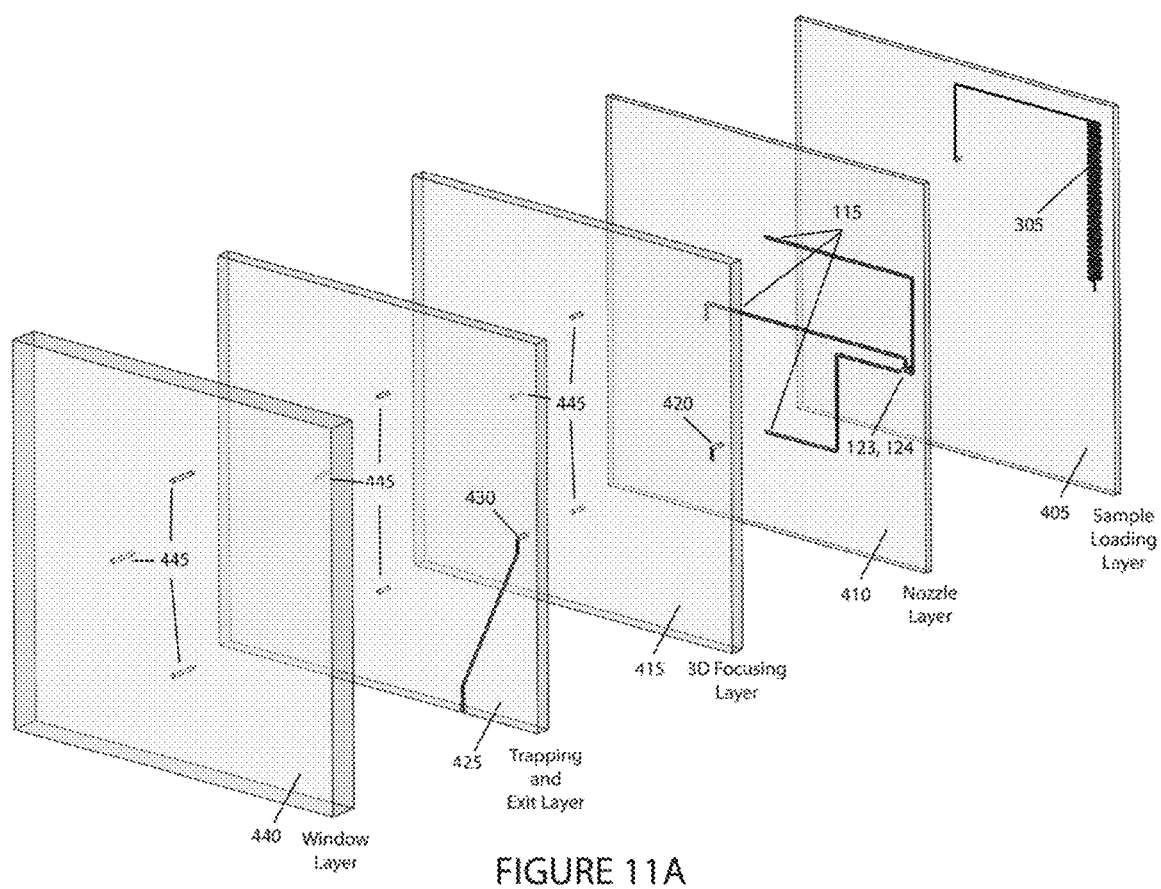
FIGS. 11A-11B are an exploded perspective view and a collapsed perspective view, respectively, of an illustrative embodiment of the instant invention.

An embodiment of the instant invention involves the combination of several of the above-mentioned design elements discussed above in a unitary device. An example of such a unitary device is illustrated in FIGS. 11A-1B. The illustrated embodiment of the invention is a 5-layer structure with all five layers, bonded to each other, to yield a solid microfluidic chip 400. The chip could be constructed using a number of standard materials including, but not limited to, fused silica, crown glass, soda lime glass, PDMS, OSTE, polystyrene, poly(methyl)methacrylate, polycarbonate, other plastics or polymers. This chip 400 allows for sample input, hydrodynamic focusing, optical interrogation, sample exit and clear optical access for the laser light to enter and exit the interrogation region. The first "sample loading layer" 405 includes a serpentine sample injection structure 305, for example, as discussed in reference to FIGS. 10A-10B. The "nozzle layer" 410 includes three sheath inlet channels 115 and a nozzle design 123, 124 making up half of a hydrodynamic focusing design, for example, as discussed in reference to FIGS. 8A-8J. The "3D focusing layer" 415 includes a through hole 420 for flow constriction where the sheath flow and nozzle are combined to direct flow around the core inlet flow to achieve hydrodynamic focusing. The "trapping and exit layer" 425 includes another through channel 430 for sample interrogation by the laser beam 150. The "window layer" 440 is a plate that creates a clear path for the focused laser into the "trapping and exit layer". All three layers prior to the "nozzle layer" 440, 425, 415 have three through holes each 445, that in the final device connect to the inlet channels 115 in the "nozzle layer" 410. The complete microfluidic chip 400 is optionally connected to fluidic tubing and aligned in the path of a focusing laser to complete the working device.

Figures 9D, 9E:
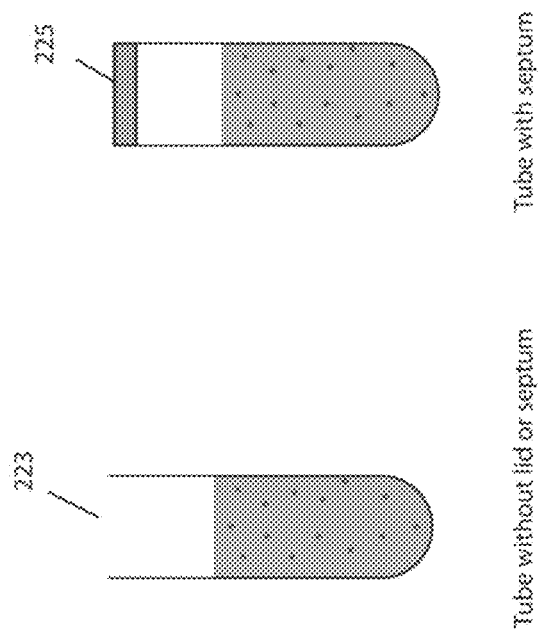
Figure 11B:
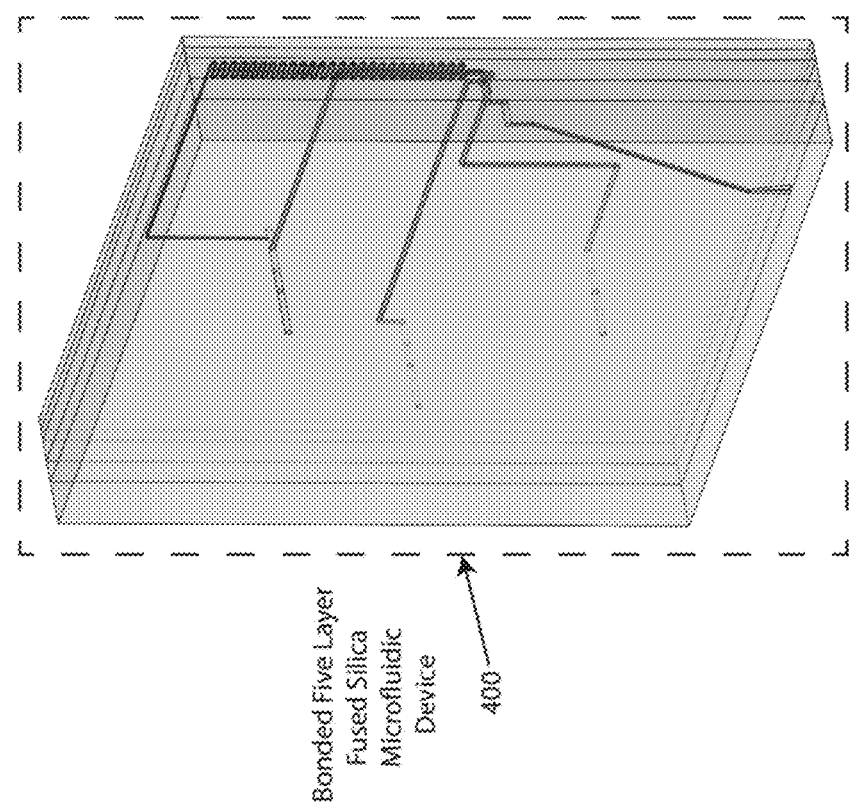
Figure 12:
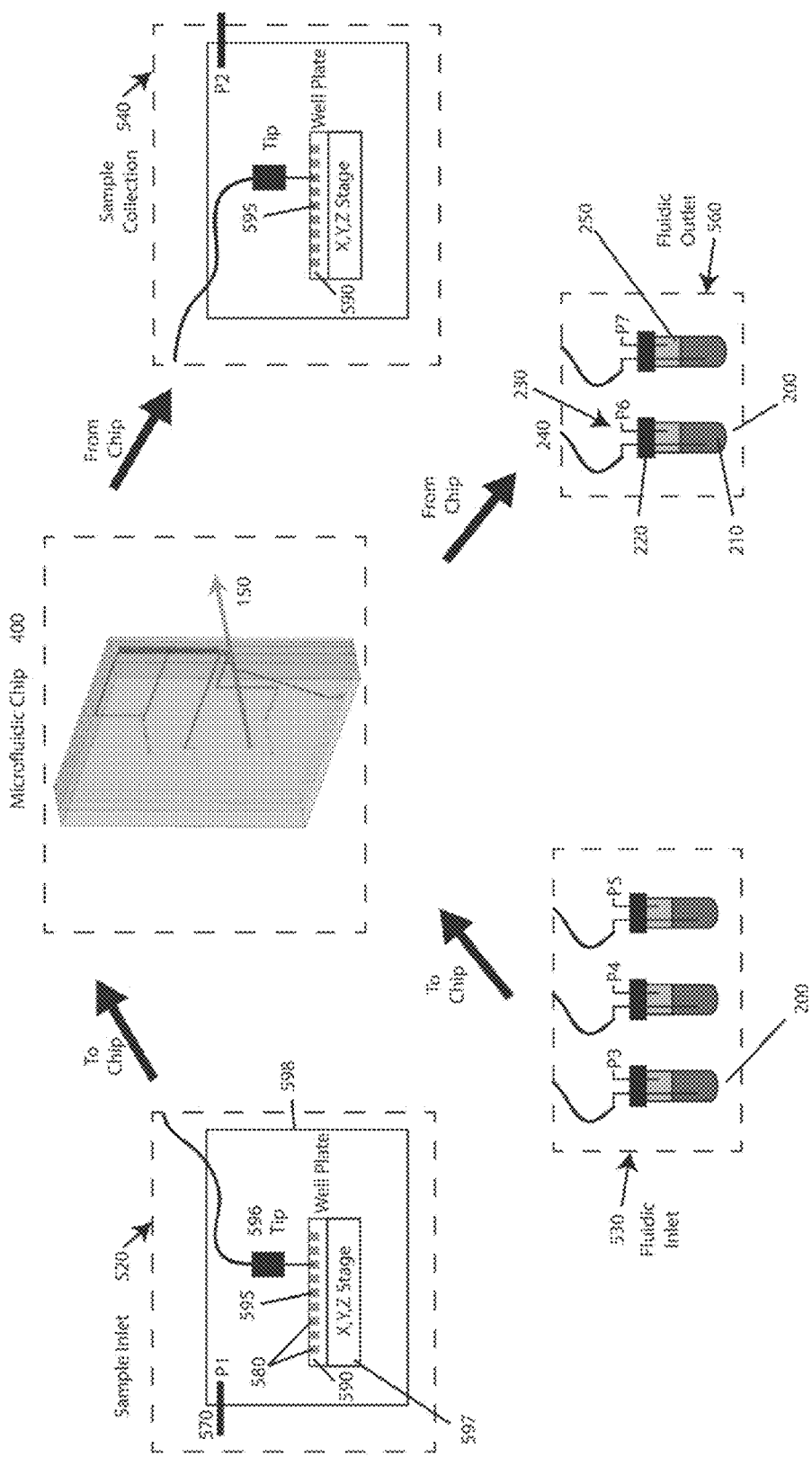
FIG. 12 is a schematic diagram of a system and a method of operation according to an illustrative embodiment of the instant invention.

An operational system schematic of an embodiment of the invention is shown, by way of example, in FIG. 12. The center of the system is comprised of the microfluidic chip 400 which is where particles encounter the laser beam 150. The chip 400 (e.g., as discussed with respect to FIGS. 11A-11B) also contains channels that serve to focus and/or sort the inlet and/or outlet flows. Attached to the chip are a number of other fluid connections that include the sample inlet 520, fluidic inlet 530, sample collection 540, and fluidic outlet 560. Both the fluidic inlet 530 and fluidic outlet 560 include one or more sealed reservoirs 200 that are fluidically connected to the chip 400. The reservoirs (e.g., as discussed with respect to FIG. 9) hold fluid 210 and have two connections in their lid 220, one for gas 230 and one for liquid 240. The gas connection 230 extends through the lid 220 and into the reservoir 200 but ends above the surface of the fluid 210 and allows gas to enter or exit the reservoir 200. The liquid connection 240 extends through the lid 220 and also ends below the surface of the sample fluid 210. Flow out of, or into, the reservoir 200 and into the chip 400 is controlled by adjusting the pressure 250 above the fluid. In the case of multiple reservoirs, the pressure above each reservoir can be independently controlled in order to achieve a precise on-chip flow pattern. The sample inlet 520 contains one or more well plate samples 580 that are pumped via pneumatic pressure 570 into the chip 400 for analysis. The sample vessel could be either a tube containing a single sample (e.g., as discussed with respect to FIG. 9), or a microfluidic well plate 590 that contains an array of samples in different reservoirs 595 (e.g., as discussed with respect to FIG. 13). The sample collection subsystem 540 will be similar to the sample inlet 520, except that it will receive samples that are pumped from the chip 400. Just as with the sample inlet 520, these collected samples 540 could be collected in a single tube or in a well plate 590 format that contains multiple collection reservoirs 595. In the case of a well plate format for either the sample inlet 520\or sample collection 540, a tip 596\will be positioned above the well plate and will serve as the interface to the chip 400. The well plate 590 will be attached to a stage 597 that can be precisely moved in three dimensions, such that the tip can move from one well to another. The sample inlet 520 or sample collection 540 could be enclosed 598 such that the pressure 570 above the entire well plate 590 and sample tip 596 can be precisely controlled.

Another embodiment of the instant invention includes a method of particle analysis and/or separation. At least one collimated light source operable to generate at least one collimated light source beam is provided. The at least one collimated light source beam includes at least one beam cross-section. A body is provided and defines a first channel in a first plane, a second channel in a second plane orthogonal to the first plane, the second channel communicating with the first channel, the second channel comprising a second channel cross-section, the second channel being oriented to receive the at least one collimated light source beam, a third channel in a third plane orthogonal to the second plane, the third channel communicating with the second channel. The at least one collimated light source beam is transmitted through the second channel, the transmitted at least one collimated light source beam comprising a beam direction. A sample flow is transmitted into the first channel. The fluid sample includes a flow direction opposite the beam direction. The sample flow includes a plurality of particles. The plurality of particles includes at least one particle type. The sample flow includes a sample flow cross-section. The sample flow cross-section includes a sample flow cross-section size. The sample flow includes a sample flow center. At least one sheath flow is transmitted into the first channel, a combined flow including the sample flow and the at least one sheath flow. Focusing the sample flow cross-section size within the combined flow and/or positioning the sample flow center within the combined flow.

Optionally, the sample flow includes a sample flow rate and the at least one sheath flow includes at least one sheath flow rate. The focusing of the sample flow cross-section size within the combined flow includes providing the at least one sheath flow rate greater than the sample flow rate.

Optionally, the at least one sheath flow includes a plurality of sheath flows. The positioning of the sample flow center within the combined flow includes providing each sheath flow of the plurality of sheath flows comprising an independent respective sheath flow rate.

Optionally, the at least one particle type includes a plurality of particle types. Each particle type of the plurality of particle types includes respective intrinsic properties and respective induced properties. Optionally, the intrinsic properties include size, shape, refractive index, morphology, intrinsic fluorescence, and/or aspect ratio. Optionally, the induced properties include deformation, angular orientation, rotation, rotation rate, antibody label fluorescence, aptamer label fluorescence, DNA label fluorescence, stain label fluorescence, a differential retention metric, and/or a gradient force metric. This method embodiment further includes identifying and separating the plurality of particles according to the respective particle types based on at least one of the intrinsic properties and the induced properties. Optionally, this method embodiment further includes interrogating the sample flow. Optionally, interrogating the sample flow includes determining at least one of the intrinsic properties and the induced properties of the particle types, and measuring particle velocity of the plurality of particles. Optionally, the at least one collimated light source beam includes at least one beam axis, and the sample flow includes a sample flow axis. The step of determining at least one of the intrinsic properties and the induced properties of the particle types, and the step of measuring particle velocity of the plurality of particles together comprise offsetting the beam axis from the sample flow axis. Optionally, the step of determining at least one of the intrinsic properties and the induced properties of the particle types, and the step of measuring particle velocity of the plurality of particles together comprise calculating a slope and a trajectory of a particle of the plurality of particles deviating from a sample flow axis toward at least one beam axis.

Optionally, the first channel 110 comprises a wall 180. The separating the plurality of particles according to the respective particle types based on at least one of the intrinsic properties and the induced properties includes retaining against the wall particles of a same particle type of the plurality of particle types.

Optionally, the second channel 120 is connected to at least one collection channel. The separating the plurality of particles according to the respective particle types based on at least one of the intrinsic properties and the induced properties comprises directing particles of a same particle type of the plurality of particle types to a respective collection channel of the at least one collection channel. Optionally, the at least one collimated light source beam 140 comprises a plurality of beams, a movable beam, and a beam with a multi-modal intensity cross-section, the at least one collection channel comprising a plurality of collection channels.

Optionally, the step of separating the plurality of particles according to the respective particle types based on the intrinsic properties and/or the induced properties includes actively separating the plurality of particles. Optionally, the third channel 130 is connected to at least one collection channel. The at least one collection channel includes at least one respective collection channel flow rate. The step of actively separating the plurality of particles includes varying the at least one respective collection channel flow rate.

Optionally, the sample flow comprises a sample flow rate, the method embodiment further includes providing a serpentine channel 305 connected to the first channel 110, the serpentine channel comprising a serpentine channel axis 306, the serpentine channel axis being parallel to a force of gravity 310, and controlling the sample flow rate within the serpentine channel to prevent particle sedimentation and loss of particle velocity within the serpentine channel.

Optionally, the method embodiment further includes providing a sample inlet line tip communicating with a sample inlet line, which communicates with the first channel. A sample well plate is provided, the sample well plate including a plurality of sample wells and/or at least one waste moat, the plurality of sample wells including a respective amount of sample. A portion of the respective amount of sample is removed from a first sample well of the plurality of sample wells by pushing the respective amount of sample by fluid pressure into the sample inlet line. The sample inlet line tip is moved to one of a next sample well of the plurality of sample wells and the at least one waste moat. Optionally, the method embodiment further includes keeping the sample inlet line tip submerged in sample, contained within the moat, during transfer from the first sample well to the next sample well.

Optionally, the third channel 130 is connected to at least one collection channel, the at least one collection channel including a respective collection channel fluid pressure. The method embodiment further includes providing an outlet tip communicating with the at least one collection channel. An outlet well plate is provided, the outlet well plate including a plurality of outlet wells and/or at least one waste moat. A respective amount of sample is added to a first outlet well of the plurality of outlet wells by pushing the respective amount of sample via the outlet tip by the respective collection channel fluid pressure. The outlet tip is moved to one of a next outlet well of the plurality of outlet wells and the at least one waste moat. Optionally, the method embodiment further includes keeping the outlet tip submerged in sample during transfer from the first outlet well to the next outlet well.

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art may effect alterations, modifications and variations to the examples without departing from the scope of the invention.

These and other implementations are within the scope of the following claims.

What is claimed as new and desired to be protected by Letters Patent of the United States is:

1. A method comprising:
    providing at least one collimated light source operable to generate at least one collimated light source beam, the at least one collimated light source beam comprising at least one beam cross-section;
    providing a body defining a first channel in a first plane, a second channel in a second plane orthogonal to the first plane, the second channel communicating with the first channel, the second channel comprising a second channel cross-section, the second channel being oriented to receive the at least one collimated light source beam, a third channel in a third plane orthogonal to the second plane, the third channel communicating with the second channel;
    transmitting the at least one collimated light source beam through the second channel, the transmitted at least one collimated light source beam comprising a beam direction;
    transmitting a sample flow into the first channel, the sample flow comprising a flow direction opposite the beam direction in the second channel, the sample flow comprising a plurality of particles, the plurality of particles comprising at least one particle type, the sample flow comprising a sample flow cross-section, the sample flow cross-section comprising a sample flow cross-section size, the sample flow comprising a sample flow center;
    transmitting at least one sheath flow into the first channel, a combined flow comprising the sample flow and the at least one sheath flow; and
    at least one of focusing the sample flow cross-section size within the combined flow and positioning the sample flow center within the combined flow.

2. The method according to claim 1, wherein the sample flow comprises a sample flow rate and the at least one sheath flow comprises at least one sheath flow rate, wherein said focusing the sample flow cross-section size within the combined flow comprises:
    providing the at least one sheath flow rate greater than the sample flow rate.

3. The method according to claim 1, wherein the at least one particle type comprises a plurality of particle types, each particle type of the plurality of particle types includes respective intrinsic properties and respective induced properties.

4. The method according to claim 3, wherein the intrinsic properties comprise at least one of size, shape, refractive index, morphology, intrinsic fluorescence, and aspect ratio.

5. The method according to claim 3, wherein the induced properties comprise at least one of deformation, angular orientation, rotation, rotation rate, antibody label fluorescence, aptamer label fluorescence, DNA label fluorescence, stain label fluorescence, a differential retention metric, and a gradient force metric, the method further comprising:

identifying and separating the plurality of particles according to the respective particle types based on at least one of the intrinsic properties and the induced properties.

6. The method according to claim 3, further comprising: interrogating the sample flow.

7. The method according to claim 6, wherein said interrogating the sample flow comprises:
determining at least one of the intrinsic properties and the induced properties of the particle types, and
measuring particle velocity of the plurality of particles.

8. The method according to claim 7, wherein the at least one collimated light source beam comprises a at least one beam axis, the sample flow comprising a sample flow axis,
wherein said determining at least one of the intrinsic properties and the induced properties of the particle types, and said measuring particle velocity of the plurality of particles together comprise offsetting the beam axis from the sample flow axis.

9. The method according to claim 8, wherein said determining at least one of the intrinsic properties and the induced properties of the particle types, and said measuring particle velocity of the plurality of particles together comprise calculating a slope and a trajectory of a particle of the plurality of particles deviating from a sample flow axis toward at least one beam axis.

10. The method according to claim 3, wherein the first channel comprises a wall,
wherein said separating the plurality of particles according to the respective particle types based on at least one of the intrinsic properties and the induced properties comprises retaining against the wall particles of a same particle type of the plurality of particle types.

11. The method according to claim 3, wherein the second channel is connected to at least one collection channel,
wherein said separating the plurality of particles according to the respective particle types based on at least one of the intrinsic properties and the induced properties comprises directing particles of a same particle type of the plurality of particle types to a respective collection channel of the at least one collection channel.

12. The method according to claim 11, wherein the at least one collimated light source beam comprises a plurality of beams, a movable beam, and a beam with a multi-modal intensity cross-section, the at least one collection channel comprising a plurality of collection channels.

13. The method according to claim 3, wherein said separating the plurality of particles according to the respective particle types based on at least one of the intrinsic properties and the induced properties comprising actively separating the plurality of particles.

14. The method according to claim 13, wherein the third channel is connected to at least one collection channel, the at least one collection channel comprising at least one respective collection channel flow rate,
wherein said actively separating the plurality of particles comprises varying the at least one respective collection channel flow rate.

15. The method according to claim 1, wherein the sample flow comprises a sample flow rate, the method further comprising:
providing a serpentine channel connected to the first channel, the serpentine channel comprising a serpentine channel axis, the serpentine channel axis being parallel to a force of gravity, and
controlling the sample flow rate within the serpentine channel to prevent particle sedimentation and loss of particle velocity within the serpentine channel.

16. The method according to claim 1, further comprising:
providing a sample inlet line tip communicating with a sample inlet line, which communicates with the first channel;
providing a sample well plate, the sample well plate comprising at least one of a plurality of sample wells and at least one waste moat, the plurality of sample wells comprising a respective amount of sample;
removing the respective amount of sample from a first sample well of the plurality of sample wells by pushing the respective amount of sample by fluid pressure into the sample inlet line; and
moving the sample inlet line tip to one of a next sample well of the plurality of sample wells and the at least one waste moat.

17. The method according to claim 16, further comprising:
keeping the sample inlet line tip submerged in sample during transfer from the first sample well to the next sample well.

18. The method according to claim 1, wherein the third channel is connected to at least one collection channel, the at least one collection channel comprising a respective collection channel fluid pressure, the method further comprising:
providing an outlet tip communicating with the at least one collection channel;
providing an outlet well plate, the outlet well plate comprising at least one of a plurality of outlet wells and at least one waste moat;
adding a respective amount of sample to a first outlet well of the plurality of outlet wells by pushing the respective amount of sample via the outlet tip by the respective collection channel fluid pressure; and
moving the outlet tip to one of a next outlet well of the plurality of outlet wells and the at least one waste moat.

19. The method according to claim 18, further comprising:
keeping the outlet tip submerged in sample during transfer from the first outlet well to the next outlet well.

20. A method comprising:
providing at least one collimated light source operable to generate at least one collimated light source beam, the at least one collimated light source beam comprising at least one beam cross-section;
providing a body defining a first channel in a first plane, a second channel in a second plane orthogonal to the first plane, the second channel communicating with the first channel, the second channel comprising a second channel cross-section, the second channel being oriented to receive the at least one collimated light source beam, a third channel in a third lane orthogonal to the second plane, the third channel communicating with the second channel;
transmitting the at least one collimated light source beam through the second channel, the transmitted at least one collimated light source beam comprising a beam direction;
transmitting a sample flow into the first channel, the sample flow comprising a flow direction opposite the beam direction in the second channel, the sample flow comprising a plurality of particles, the plurality of particles comprising at least one particle type, the sample flow comprising a sample flow cross-section, the sample flow cross-section comprising a sample flow cross-section size, the sample flow comprising a sample flow center;

transmitting at least one sheath flow into the first channel, a combined flow comprising the sample flow and the at least one sheath flow; and at least one of focusing the sample flow cross-section size within the combined flow and positioning the sample flow center within the combined flow, wherein the at least one sheath flow comprises a plurality of sheath flows, said positioning the sample flow center within the combined flow comprises providing each sheath flow of the plurality of sheath flows comprising an, independent respective sheath flow rate.

* * * * *